US006919178B2

(12) United States Patent
Erlanson et al.

(10) Patent No.: US 6,919,178 B2
(45) Date of Patent: Jul. 19, 2005

(54) EXTENDED TETHERING APPROACH FOR RAPID IDENTIFICATION OF LIGANDS

(75) Inventors: Daniel A. Erlanson, San Francisco, CA (US); Andrew C. Braisted, San Francisco, CA (US); Robert McDowell, San Francisco, CA (US); John Prescott, San Francisco, CA (US)

(73) Assignee: Sunesis Pharmaceuticals, Inc., South San Francisco, CA (US)

(*) Notice: Subject to any disclaimer, the term of this patent is extended or adjusted under 35 U.S.C. 154(b) by 31 days.

(21) Appl. No.: 09/990,421

(22) Filed: Nov. 21, 2001

(65) Prior Publication Data

US 2002/0150947 A1 Oct. 17, 2002

Related U.S. Application Data

(60) Provisional application No. 60/252,294, filed on Nov. 21, 2000, and provisional application No. 60/310,725, filed on Aug. 7, 2001.

(51) Int. Cl.[7] .................................................. C12Q 1/68
(52) U.S. Cl. ................................ 435/6; 435/4; 435/7.1
(58) Field of Search ................ 435/4–6, 7.1, DIG. 2–3, 435/22, 34

(56) References Cited

U.S. PATENT DOCUMENTS

| 4,946,778 A | 8/1990 | Ladner et al. ............. 435/69.6 |
| 5,367,058 A | 11/1994 | Pitner et al. ............. 530/391.9 |
| 5,422,281 A | 6/1995 | Harris et al. ................ 436/501 |
| 5,571,681 A | 11/1996 | Janda ......................... 435/7.6 |
| 5,783,384 A | 7/1998 | Verdine ......................... 535/6 |
| 5,958,702 A | 9/1999 | Benner ....................... 435/7.1 |

FOREIGN PATENT DOCUMENTS

| EP | 0 801 307 | 10/1997 | |
| WO | WO 95/18972 | 7/1995 | |
| WO | WO 95/25737 | 9/1995 | |
| WO | WO 96/13613 | 5/1996 | |
| WO | WO 96/27605 | 9/1996 | |
| WO | WO 97/12897 | 4/1997 | |
| WO | WO 97/35202 | 11/1997 | |
| WO | WO 97/43302 | 11/1997 | |
| WO | WO 98/11436 | * 3/1998 | .......... G01N/33/53 |
| WO | WO 98/11437 | 3/1998 | |
| WO | WO 98/15969 | 4/1998 | |
| WO | WO 98/25146 | 6/1998 | |
| WO | WO 98/56028 | 12/1998 | |
| WO | WO 99/49314 | 9/1999 | |
| WO | WO 99/50668 | 10/1999 | |
| WO | WO 99/50669 | 10/1999 | |
| WO | WO 99/63944 | 12/1999 | |
| WO | WO 00/00823 | 1/2000 | .......... G01N/33/53 |
| WO | WO 00/03240 | 1/2000 | |
| WO | WO 01/02856 | 1/2001 | |

OTHER PUBLICATIONS

Erlanson, D. A.; Braisted, A. C.; Raphael, D. R.; Randal, M.; Stroud, R. M.; Gordon, E. M.; Wells, J. A. "Site–directed ligand Discovery" PNAS Aug. 15, 2000, 97(17), 9367–9372) (Paper No. 5, IDS Reference 29.*

Hajduk et al. "Discovery of Potent Nonpeptide Inhibitors of Stromelysin Using SAR by NMR" J. Am. Chem. Soc. 1997, 119, 5818–5827.*

Bella, J., et al., "The structure if the two amino–terminal domains of human ICAM–1 suggests how it functions as a rhinovirus receptor and as an LFA–1 integrin ligand", Proc. Natl. Acad. Sci. USA, vol. 95, No. 8, pp 4140–4145, Apr. 1998.

Berman, H. M., et al. , "The Protein Data Bank", Nucleic Acids Research, vol. 28, No. 1, pp 235–242, 2000.

Brady Jr., G. Patrick, et al., "Fast prediction and visulatization of protein binding pockets with PASS", Journal of Computer Aided Molecular Designs, vol. 14, pp 383–401, 2000.

Bravo, Jerónimo, et al., "Crystal structure of a cytokine–binding region of gp 130", The Embo Journal, vol. 17, No. 6, pp. 1665–1674, 1998.

Brown, Nick R., et al., "The structural basis for specificity of substrate and recruitment peptides for cyclin–dependent kinases", Nature Cell Biology, vol. 1, pp 438–443, Nov. 1999.

Burlingame, A.L., et al., "Mass Spectrometry", Analytical Chemistry, vol. 68, No. 12, pp 599R–651R, Jun. 1996.

Cerretti, Douglas Pat, et al., "Molecular Cloning of the Interleukin–1β Converting Enzyme", Science, vol. 356, pp 97–100, Apr. 1992.

Cha, Sun–Shin, et al., "Crystal Structure of TRAIL–DR5 Complex Identifies a Critical Role of the Unique Frame Insertion in Conferring Recognition Specificity", J Biol. Chem., vol. 275, No. 40, pp 31171–31177, 2000.

Cha, Sun–Shin, et al., "2.8 Å Resolution Crystal Structure of Human TRAIL, a Cytokine with Selective Antitumor Activity", Immunity, vol. 11, No. 2, pp 253–261, Aug. 1999.

Chan, David C., et al., "Core Structure of gp41 from the HIV Envelope Glycoprotein", Cell, vol. 89, No. 2, pp 263–273, Apr. 1997.

Chen, Julian, C.–H., et al., "Crystal structure of the HIV–1 integrase catalytic core and C–terminal domains: A model for viral DNA binding", PNAS USA, vol. 97, No. 15, pp 8233–8238, Jul. 2000.

(Continued)

Primary Examiner—Andrew Wang
Assistant Examiner—Jon D. Epperson
(74) Attorney, Agent, or Firm—Ginger R. Dreger, Esq.; Heller Ehrman, LLP

(57) ABSTRACT

The invention concerns a method for rapid identification and characterization of binding partners for a target molecule, and for providing binding partners with improved binding affinity. More specifically, the invention concerns an improved tethering method for the rapid identification of at least two binding partners that bind near one another to a target molecule.

27 Claims, 6 Drawing Sheets

OTHER PUBLICATIONS

Chothia, Cyrus, "The Nature of the Accessible and Buried Surfaces in Proteins", J. Molecular Biol., vol. 105, pp 1–14, 1976.

Chow, Dar Chone, et al., "Structure of an Extracellular gp130 Cytokine Receptor Signaling Complex", Science, vol. 291, pp 2150–2155, Mar. 2001.

Chu, Yen Ho, et al, "Affinity Capillary ElectrophoresisMass Spectrometry for Screening Combinatorial Libraries", J. Am. Chem. Soc., vol. 118; pp 7827–7835, 1996.

Clackson, Tim, et al., "A High Spot of Binding Energy in Hormone–Receptor Interface", Science, vol. 267, pp 383–386, Jan. 1995.

Cohen G.M., "Caspases: the executioner of apoptosis", Biochem. J, vol. 326, pp 1–16, 1997.

Connolly, Michael L., "Solvent–Accessible Surfaces of Proteins and Nucleic Acids", Science, vol. 221, No. 4612, pp 709–713, 1983.

Cosenza, Larry, et al., "Comparative model building of interleukin–7 using interleukin–4 as a template: A structural hypothesis that displays atypical surface chemistry in helix D important for receptor activation", Protein Science, vol. 9, pp 916–926, 2000.

Creamer, Trevor P., et al, "Modeling Unfolded States if Peptides and Proteins", Biochemistry, vol. 34, pp 61245–16250, 1995.

Creighton, Thomas E.., Proteins: Structures and Molecular Principles, W.H. Freeman & Co, N.Y., pp 239–245, 1983.

Cunningham, Brian C. et al., "Comparison of a Structural and a Functional Epitope", J. Mol. Biol., vol. 234, pp 554–563, 1993.

Cunningham, Brian C., et al., "High–Resolution Epitope Mapping of hGH–Receptor Interactions by Alanine–Scanning Mutagenesis", Science, vol. 244, pp. 1081–1085, Jun. 1989.

Davies, Gregg, et al, "Use of a Diimidoester Cross–Linking Reagent to Examine the Subunit Structure of a Rabbit Muscle Private Kinase[1]", Canadian J. Biochem., vol. 50, pp 416–422, 1972.

Dessen, Andrea, et al., "Crystal Structure of Human Cytosolic Phospholipase $A_2$ Reveals a Novel Topology and Catalytic Mechanism", Cell, vol. 97, pp 349–360, Apr. 1999.

Di Marco, Stefania, et al., "Inhibition of the Hepatitis C Virus NS3/4A Protease", J. Biol. Chem, vol. 275, No. 10, pp 7152–7257, 2000.

Duncan, Bruce S., et al., "Approximation and Characterization of Molecular Surfaces", Biopolymers, vol. 33, pp 219–229, 1993.

Eck, Michael J., et al., "The Structure of Tumor Necrosis Factor–α at 2.6 Å Resolution", J Biol. Chem, vol. 264, No. 29, pp 17595–17605, 1989.

Ede, Nicholas J., et al., "A Simple Linker for the Attachment of Aldehydes to the Solid Phase. Application to Solid Phase Synthesis by the Multipin™ Method", Tetrahedron Letters, vol. 38, No. 40, pp 7119–7122, 1997.

Eigenbrot, Charles, et al., "The Factor VII Zymogen Structure Reveals Registration of β Strands during Activation", Structure, vol. 9, pp 627–636, 2001.

Ettmayer, P. et al, "Structural and Conformational Requirements for High–Affinity Binding to the SH2 Domain of Grb2[1]", J. Med. Chem., vol. 42, No. 6, pp 971–980, 1999.

Fengler, Annett, et al., "Three–dimensional structures of the cysteine proteases cathepsins K and S deduced by knowledge–based modeling and active site characteristics", Protein Engineering, vol. 11, No. 11, pp 1007–1013, 1998.

Finer–Moore, Janet S., et al., "Solvent Structure in Crystals of Trypsin Determined by X–Ray and Neutron Diffraction", Proteins: Structure, Function and Genetics, vol. 12, pp 203–222, 1992.

Fitzgerald Michael, et al. "Biochemical mass spectrometry: worth the weight", Chemistry & Biology, vol. 3, pp 707–715, Sep. 1996.

Garman, Scott, C. et al., "Crystal Structure of the Human High–Affinity IgE Receptor", Cell, vol. 95, pp 951–961, Dec. 1998.

Garman, Scott, C. et al., "Structure of the Fc fragment of human IgE bound to its high–affinity receptor FcεRIα", Nature, vol. 406, pp 259–266, Jul. 1998.

Gerber, Nancy, et al., "Receptor–Binding Conformation of the 'ELR' Motif of IL–8: X–Ray Structure of the L5C/H33C Variant at 2.35 Å Resolution", pp 361–367, 2000.

Grubbs, Robert H., et al., "Ring–Closing Metathesis and Related Processes in Organic Synthesis", Acc. Chem. Res., vol. 28, pp. 446–453, 1995.

Hage, Thorsten, et al., "Crystal Structure of the Interleukin–4/Receptor α Chain Complex Reveals a Mosaic Binding Interface", Cell, vol. 97, pp 271–281, 1999.

Hobohm, Uwe, et al, "Selection of representative protein data sets", Protein Science, vol. 1, pp 409–417, 1992.

Hong, Lin, et al., "Structure of the Protease Domain of Memapsin 2 (β–Secretase) Complexed with Inhibitor", Science, vol. 290, pp 150–153, Oct. 2000.

Hymowitz, Sarah, et. al., "A Unique Zinc–Binding Site Revealed by a High Resolution X–ray Structure of Homotrimeric Apo2L/TRAIL", Biochemistry, vol. 39, pp 633–640, 2000.

Ikemizu, Shinji, et al, "Structure and Dimerization of a Soluble Form of B7–1", Immunity, vol. 12, pp 51–60, Jan. 2000.

Karpusas, M. et al, "2 Å crystal structure of an extracellular fragment of human CD40 ligand", Structure, vol. 3, No. 12, p. 1426, 1995.

Kussie, Paul H., et al, "Structure of the MDM2 Oncoprotein Bound to the p53 Tumor Suppressor Transactivation Domain", Science, vol. 274, pp 948–953, Nov. 1996.

Lee, B. et al., "The Interpretation of Protein Structures: Estimation of Static Accessibility", J Mol. Biol., vol. 55, pp 379–400, 1971.

Liang, Jun, et al., "Refined structure of the FKBP12–rapamycin–FRB ternary complex at 2.2 Å resolution", Acta Crystallographica Section D, D55, pp 736–744, 1999.

Loo, Joseph A., et al., "Chapter 32: Application of Mass Spectrometry for Characterizing and Identifying Ligands from Combinatorial Libraries", Annual Reports in Medicinal Chemistry, vol. 31, pp 319–325, 1996.

Lubowski, Jacek, et al., "The Structure of MCP–1 in two crystal forms provides a rare example of variable quaternary interactions", Nature Structural Biology, vol. 4, No. 1, pp 64–69, Jan. 1997.

Maignan, Sébastein, et al, "Crystal Structure of the Mammalian Grb2 Adaptor", Science, vol. 268, pp 291–293, Apr. 1995.

Maignan, Sébastein, et al., "Crystal Structures of the Catalytic Domain of HIV–1 Integrase Free and Complexed with its Metal Codfactor: High Level of Similarity of the Active Site with Other Viral Integrases", J. Mol. Biol., vol. 282, pp 359–68, 1998.

March, Jerry, Advanced Organic Chemistry: Reactions, Mechanisms and Structure:, John Wiley & Sons, New York, 4th Edition, pp. 898–900, 1276, 904–906, 1275, 1299, 892, 1280, 1296, 1297, 1284, 1285, 1281, 368, 1269, 392, 1264, 1146–1148, 1992.

Maskos, Klaus, et al, "Crystal structure of the catalytic domain of human tumor necrosis factor–α–converting enzyme", PNAS, vol. 95, pp 3408–3412, Mar. 1998.

Matthews, D.A., et al, "Structure–assisted a design of mechanism–based irreversible inhibitors of human rhinovirus 3C protease with potent antiviral activity against multiple rhinovirus serotypes", Proc Natl. Sci. USA, vol. 96, pp 11000–11007, Sep. 1999.

McGrath, Mary E., et al, "Crystal structure of human cathepsin K complexed with a potent inhibitor", Nature Structural Biology, vol. 4, No. 2, pp 105–109, Feb. 1997.

Milburn, Michael V., et al., A novel dimer configuration revealed by the crystal structure at 2.4 Å resolution of human interleukin–5 Nature, vol. 363, pp 172–176, 1993.

Mittl. Peer R.E., et al, "Structure of Recombinant Human CPP32 in Complex with the Tetrapeptide Acetyl–Asp–Val–Ala–Asp Fluoromethyl Ketone", J. Biol. Chem., vol. 272, No. 10, pp 6539–47, Mar. 1997.

Miyaura, Noria, et al., "Palladium–Catalyzed Cross–Coupling Reactions of Organoboron Compounds", Chem. Rev., vol. 95, pp 2457–2483, 1995.

Mohammadi, Moosa, et al., "Structure of the FGF Receptor Tyrosine Kinase Domain Reveals a Novel Autoinhibitory Mechanism", Cell, vol. 86, pp 577–587, Aug. 1996.

Molteni, Valentina, et al., "Identification of a small–molecule binding site at the dimmer interface of the HIV integrase catalytic domain", Acta Crystallographica Section D, Biological Crystallography, vol. 57, pp 536–544, 2001.

Muller, Thomas, et al., "Human Interleukin–4 and Variant R88Q: Phasing X–ray Diffraction Data by Molecular Replacement Using X–ray and Nuclear Magnetic Resonance Models", J. Mol. Biol., vol. 247, No. 2, pp 360–372, 1995.

Muller, Yves A., et al, "The Crystal Structure of the Extracellular Domain of Human Tissue Factor Refined to 1.7 Å Resolution", J. Mol. Biol., vol. 256, No. 1, pp 144–159, 1996.

Ni, Chao–Zhou, et al., "Molecular basis for CD40 signaling mediated by TRAF3", Proc. Natl. Acad, Sci USA, vol. 97, No. 19, pp 10395–10399, 2000.

Nicholls, Anthony, et al, "Protein Folding and Association: Insights From the Interfacial and Thermodynamic Properties of Hydrocarbons", Proteins, vol. 11, pp. 281–296, 1991.

Okamoto, Yoshinori, et al., "Peptide Based Interleukin–1β Converting Enzyme (ICE) Inhibitors: Synthesis, structure Activity Relationships and Crystallographic Study of the ICE–inhibitor Complex", Chem. Pharm. Bull. vol. 47, No. 1, pp 11–21, Jan. 1999.

Oikonomakos, NG, et al, "A new allosteric site in glycogen phosphorylase b as a target for drug interactions", Structure, vol. 8, pp 575–584, 2000.

Parlow, et al,"Discovery of a herbicidal lead using polymer–bound activated esters in generating a combinatorial library of amides and estes", Molecular Diversity, vol. 1, pp 266–269, 1995.

Pátek, Marcel, et al., "Solid–Phase Synthesis of 'Small' Organic Molecules Based on Thiazolidine Scaffold", Tetrahedron Letters, vol. 36, No. 13, pp 2227–2230, 1995.

Pereira, Pedro J., et al, "Human β–tryptase is a ring–like tetramer with active sites facing a central pore", Nature, vol. 392, pp 306–311, Mar. 1998.

Plotnikov, Alexander N., et al, "Crystal Structures of Two FGH–FGFR Complexes Reveal the Determinants of Ligand–Receptor Specificity", Cell, vol. 101, pp 413–424, May 2000.

Plotnikov, Alexander N. et al, , "Structural Basis for FGF Receptor Dimerization and Activation", Cell, vol. 98, pp 641–650, Sep. 1999.

Plotnikov, Alexander N., et al., "Crystal Structure of Fibroblast Growth Factor 9 Reveals Regions Implicated in Dimerization and Autoinhibition", J. Biol. Chem., vol. 276, No. 6, pp 4322–4329, 2001.

Qin, Hongxu, et al., "Structural basis of procaspase–9 recruitment by the apoptotic protease–activating factor 1", Nature, vol. 399, pp 549–557, Jun. 1999.

Qu, Aidong, et al., "Crystal structure of the I–domain from the CD11a/CD18 (LFA–1, $\alpha_L\beta2$) integrin", Proc. Natl. Acad. Sci. USA, vol. 92, No. 22, pp 10277–10281, Oct. 1995.

Rahuel, Joseph, et al, "Structural basis for the high affinity of amino–aromatic SH2 phosphopeptide ligands", J. Mol. Biol, vol. 279, pp 1013–1022, 1998.

Ramachandran, G.N. et al., "Stereochemistry of polypeptide chain configurations", J. Mol. Biol., vol. 7, pp 95–99, 1962.

Ramachandran, G.N., et al, "Conformation of polypeptides and proteins", Prot. Chem., vol. 23, pp 283–437, 1968.

Richmond, Timothy J., "Solvent accessible surface area and excluded volume in proteins—Analytical equations for overlapping spheres and implications for the hydrophobic effect", J. Mol. Biol., vol. 178, pp 63–89, 1984.

Shiau, Andrew K., et al, "The structural basis of estrogen receptor/coactivator recognition and the antagonism of this interaction by tamoxifen", Cell, vol. 95, pp 927–937, Dec. 1998.

Shrake, A., et al., "Environment and Exposure to Solvent of Protein Atoms. Lysozyme and Insulin", J. Mol. Biol., vol. 79, pp 351–371, 1973.

Siudzak, Gary, "The emergence of mass spectrometry in biochemical research", Proc. Natl. Acad. Sci. USA, vol. 91, pp 11290–11297, 1994.

Sommers, William, et al, "1.9 Å crystal structure of interleukin–6: implications for a novel mode of receptor dimerization and signaling", The EMBO Journal, vol. 16, No. 5, pp 989–997, 1997.

Taylor, Neil R., et al., "Dihydropyrancarboxamides Related to Zanamivir: A New Series of Inhibitors of Influenza Virus Sialidases. 2. Crystallographic and Molecular Modeling Study of Complexes of 4–amino–4H–pyran–6–carboxamides and Sialidase from Influenza Virus Types A and B", J. Med. Chem., vol. 41, pp 798–807, 1998.

Thornburry, Nancy A., et al, "A novel heterodimeric cysteine protease is required for interleukin–1β processing in monocytes", Nature, vol. 356, pp 768–774, 1992.

Tong, Liang, et al., "Crystal Structures of the Human p56$^{lck}$ SH2 Domain in Complex with Two Short Phosphotyrosyl Peptides at 1.0 Å and 1.8 Å Resolution", J. Mol. Biol., vol. 256, No. 3, pp 601–610, 1996.

Verdecia, M.A. et al, "Structure of the human anti–apoptotic protein surviving reveals a dimeric arrangement", Nature Structural Biology, vol. 7, No. 7, pp 602–608, Jul. 2000.

Vigers, Guy P.A., et al, "X–ray Crystal Structure of a Small Antagonist Peptide Bound to Interleukin–1 Receptor Type 1", J. Biol. Chem., vol. 275, No. 47, pp 36927–36933, 2000.

Wang, Zhulun, et al., "The structure of mitogen–activated protein kinase p38 at 2.1–Å resolution", Proc. Natl. Acad. Sci., vol. 94, pp 2327–2332, Mar. 1997.

Wiesmann, Christian, et al., "Crystal Structure at 1.7 Å Resolution of VEGF Complex with Domain 2 of the Flt–1 Receptor", Cell, vol. 91, pp 695–704, Nov. 1997.

Williams, Shawn P., et al., "Atomic structure of progesterone complexed with its receptor", Nature, vol. 393, pp 392–396, May 1998.

Wu, Jiangye, et al, "Quantitative electrospray mass spectrometry for the rapid assay of enzyme inhibitors", Chemistry & Biology, vol. 4, pp 653–657, Sep. 1997.

Wu, Hao, et al., "Kinetic and structural analysis of mutant CD4 receptors that are defective in H IV gp120 binding", Proc. Natl. Acad. Sci. USA, vol. 93, pp. 15030–15035, Dec. 1996.

Xu, W. et al, "Crystal Structures of c–Src Reveal Features of Its Autoinhibitory Mechanism", Molecular Cell, vol. 3, pp 629–638, May 1999.

Xu, Robert X., et al, "Atomic Structure of PDE4: Insights into Phosphodiesterase Mechanism and Specificity", Science, vol. 288, pp 1822–1825, Jun. 2000.

Xu, G. et al, "Covalent inhibition revealed by the crystal structure of the caspase–8/p35 complex", Nature, vol. 410, pp 494–497, Mar. 2001.

Yao, Nanhua, et al., "Structure of the hepatitis C virus RNA helicase domain", Nature Structural Biology, vol. 4, No. 6, pp 463–467, Jun. 1997.

Ye, Hong, et al, "The Structural Basis for the Recognition of Diverse Receptor Sequences by TRAF2Mol", Cell, vol. 4, pp 321–330, Sep. 1999.

Abraham, D.J. et al., "How Allosteric Effectors Can Bind to the Same Protein Residue and Produce Opposite Shifts in the Allosteric Equilibrium" Biochemistry 34:150006–15020 (1995).

Boyiri, T. et al., "Bisaldehyde Allosteric Effectors as Molecular Ratchets and Probes", Biochemistry 34:10521–10536 (1995).

Bunyapaiboonsri et al., "Dynamic Deconvolution of a Pre–Equilibrated Dynamic Combinatorial Library of Acetylcholinesterase Inhibitors" ChemBioChem 2:438–444 (2001).

DeJarias et al., "Use of X–ray Co–crystal Structures and Molecular Modeling to Design Potent and Selective Non–peptide Inhibitors of Cathepsin K" J. Am. Chem. Soc. 120(35):9114–9115 (1998).

Erlanson et al., "Site–Directed ligand discovery" PNAS 97(17):9367–9372 (Aug. 15, 2000).

Foroozesh et al. "Aryl Acetylenes as Mechanism–Based Inhibitors of Cytochrome P450–Dependent Monooxugenase Enzymes" Chem. Res. Toxicol. 10(1):91–102.

Hopkins et al., "Suicide Inhibitor of Cytochrome P450 1A1 and P450 2B1" Biochem. Pharmacol. 44(4):787–796 (1992).

Huc and Lehn, "Virtual combinatorial libraries: Dynamic generation of molecular and supramolecular diversity by self–assembly" Proc. Natl. Acad. Sci. USA 94:2106–2110 (Mar. 1997).

Jones and Thornton, "Principles of protein–protein interactions" Proc. Natl. Acad. Sci. USA 93:13–20 (Jan. 1996).

Lehn, Jean–Marie, "Dynamic Combinatorial Chemistry and Virtual Combinatorial Libraries" Chem. Eur. J. 5(9)2455–2463 (1999).

Maly et al., "Combinatorial target–guided ligand assembly: identification of potent sybtype–selective c–Src inhibitors", PNAS 97(6):2419–2424 (Mar. 14, 2000).

Mathews et al., "N–Alkylaminobenzotriazoles as Isozyme–Selective Suicide Inhibitors of Rabbit Pulmonary Microsomal Cytochrome P–450" Mol. Pharmacol. 39(10):25–32 (1986).

Misumi et al., "The p2 $^{gag}$ Peptide, AEAMSQVTNTATIM, Processed for HIC–1 Pr55 $^{gag}$ was found to be a Suicide Inhibitor of HIV–1 Protease" Biochem. Biophys. Res. Commun. 241(2):275–280.

Nicolaou et al., "Combinatorial Synthesis Through Disulfide Exchange: Discovery of Potent Psammaplin A type Antibacterial Agents Active against Methicillin–Resistant Staphyloциccus aureus (MRSA)" Chem. Eur. J. 7(19):4280–4295 (2001).

Nicolaou et al., "Synthesis and Biological Evaluation of Vancomycin Dimers with Potent Activity against VANCO-MYCIN–Resistant Bactewria: Target–Accelarated Combinatorial Synthesis" Chem Eur, J. 7(17):2824–2843 (2001).

Pollack, S.J. et al., "Introduction of Nucelophines and Spectotroscopic Probes into Antibody Combining Sites" Science 242:1038–1040 (1988).

Ramstrom and Lehn, "In Situ Generation and Screening of a Dynamic Combinatorial Carbohydrate Library against Concanavalin A" ChemBioChem 1:41–48 (2000).

Sannes–Lowery et al., Trends Anal. Chem 19(8):481–491 (2000).

Shuker et al., "Discovering High–Affinity Ligands for Proteins: SAR by NMR" Science 274(5292):1531 (Nov. 1996).

Stanojevic and Verdine, "Deconstruction of GCN4/GCRE into a monomeric peptide–DNA complex" Nature Structural Biology 2(6):450–457 (Jun. 6, 1995).

Thompson et al., "Design of a potent and selective human cathespin K inhibitors that spans the active site", Proc. Natl. Acad. Sci USA 94:14249014254 (1997).

Wetterau et al., "An MTP Inhibitor That Normalizes Atherogenic Lipprotein Levels in WHHL Rabbists" Science 282:751–754 (Oct. 23, 1998).

Woodcroft et al., "N–Aralkylated derivatives of 1–aminobenzotriazole as isozyme–selective mechanism–based inhibitors of guinea pig hepatic cytochrome P–450 dependent monooxygenase activity" Can. J. Physiol. Pharmacol. 68(9):1278–1285 (1990).

Zhang et al., "Covalent Modification and Active Site–Directed Inactivation of a low Molecular Weight Phosphotyrosyl Protein Phosphatase" Biochemistry 31(6):1701–1711 (1992).

* cited by examiner

FIG. 3 "Dynamic" Extended Tethering Strategy

EXTENDED TETHERING APPROACH FOR RAPID IDENTIFICATION OF LIGANDS

This application claims priority under 35 U.S.C. § 1.19 (e) of U.S. Provisional Application No. 60/252,294 filed on Nov. 21, 2000 and U.S. Provisional Application No. 60/310,725 filed on Aug. 7, 2001.

BACKGROUND OF THE INVENTION

1. Field of the Invention

The present invention relates generally to a method for rapid identification and characterization of binding partners for a target molecule, and for providing modified binding partners with improved binding affinity. More specifically, the invention concerns an improved tethering method for the rapid identification of small molecule fragments that bind near one another on a target molecule. The method is particularly suitable for rapid identification of small molecule ligands that bind weakly near sites of interest through a preformed linker on a target biological molecule (TBM), such as a polypeptide or other macromolecule, to produce higher affinity compounds.

2. Description of the Related Art

The drug discovery process usually begins with massive screening of compound libraries (typically hundreds of thousands of members) to identify modest affinity leads ($K_d$ ~1 to 10 $\mu$M). Although some targets are well suited for this screening process, most are problematic because moderate affinity leads are difficult to obtain. Identifying and subsequently optimizing weaker binding compounds would improve the success rate, but screening at high concentrations is generally impractical because of compound insolubility and assay artifacts. Moreover, the typical screening process does not target specific sites for drug design, only those sites for which a high-throughput assay is available. Finally, many traditional screening methods rely on inhibition assays that are often subject to artifacts caused by reactive chemical species or denaturants.

Erlanson et al., *Proc. Nat. Acad Sci. USA* 97:9367–9372 (2000), have recently reported a new strategy, called "tethering", to rapidly and reliably identify small (~250 Da) soluble drug fragments that bind with low affinity to a specifically targeted site on a protein or other macromolecule, using an intermediary disulfide "tether." According to this approach, a library of disulfide-containing molecules is allowed to react with a cysteine-containing target protein under partially reducing conditions that promote rapid thiol exchange. If a molecule has even weak affinity for the target protein, the disulfide bond ("tether") linking the molecule to the target protein will be entropically stabilized. The disulfide-tethered fragments can then be identified by a variety of methods, including mass spectrometry (MS), and their affinity improved by traditional approaches upon removal of the disulfide tether. See also PCT Publication No. WO 00/00823, published on Jan. 6, 2000.

Although the tethering approach of Erlanson et al. represents a significant advance in the rapid identification of small low-affinity ligands, and is a powerful tool for generating drug leads, there is a need for further improved methods to facilitate the rational design of drug candidates.

SUMMARY OF THE INVENTION

The present invention describes a strategy to rapidly and reliably identify ligands that have intrinsic binding affinity for different sites on a target molecule by using an extended tethering approach. This approach is based on the design of a Small Molecule Extender (SME) that is tethered, via a reversible or irreversible covalent bond, to a Target Molecule (TM) at or near a first site of interest, and has a chemically reactive group reactive with small organic molecules to be screened for affinity to a second site of interest on the TM. Accordingly, the SME is used for screening a plurality of ligand candidates to identify a ligand that has intrinsic binding affinity for a second site of interest on the TM. If desired, further SME's can be designed based on the identification of the ligand with binding affinity for the second site of interest, and the screening can be repeated to identify further ligands having intrinsic binding affinity for the same or other site(s) of interest on the same or related TM's.

One aspect of the invention concerns the design of a Small Molecule Extender (SME). In this aspect, the invention concerns a process comprising:

(i) contacting a Target Molecule (TM) having a first and a second site of interest, and containing or modified to contain a reactive nucleophile or electrophile at or near the first site of interest with a plurality of first small organic ligand candidates, the candidates having a functional group reactive with the nucleophile or electrophile, under conditions such that a reversible covalent bond is formed between the nucleophile or electrophile and a candidate that has affinity for the first site of interest, to form a TM-first ligand complex;

(ii) identifying the first ligand from the complex of (i); and (iii) designing a derivative of the first ligand identified in (ii) to provide a SME having a first functional group reactive with the nucleophile or electrophile on the TM and a second functional group reactive with a second ligand having affinity for the second site of interest.

In one embodiment of this aspect of the invention, the SME of step (iii) above is designed such that it is capable of forming an irreversible covalent bond with the nucleophile or electrophile of the TM. In a preferred embodiment, the reactive group on the TM is a nucleophile, preferably a thiol, protected thiol, reversible disulfide, hydroxyl, protected hydroxyl, amino, protected amino, carboxyl, or protected carboxyl group, and preferred first functional groups on the SME are groups capable of undergoing SN2-like additions or forming Michael-type adducts with the nucleophile. SME's designed in this manner are then contacted with the TM to form an irreversile TM-SME complex. This complex is then contacted with a plurality of second small organic ligand candidates, where such candidates have a functional group reactive with the SME in the TM-SME complex. As a result, a candidate that has affinity for the second site of interest on the TM forms a reversible covalent bond with the TM-SME complex, whereby a ligand having intrinsic binding affinity for the second site of interest is identified.

In an alternative embodiment of the invention, the SME of step (iii) above is designed to contain a first functional group that forms a first reversible covalent bond with the nucleophile or electrophile on the TM. The reactive group on the TM preferably is a nucleophile. The reversible covalent bond preferably is a disulfide bond which is formed with a thiol, protected thiol, or reversible disulfide bond on the TM. SME's designed in this manner are then contacted with the TM either prior to or simultaneously with contacting the TM with a plurality of second small organic ligand candidates, each small organic ligand candidate having a free thiol, protected thiol, or a reversible disulfide group, under conditions of thiol exchange, wherein a ligand candidate having affinity for the second site of interest on the TM forms a disulfide bond with the TM-SME complex, whereby a second ligand is identified. The process may be performed in the presence of a disulfide reducing agent, such as mercaptoethanol, dithiothreitol (DTT), dithioerythreitol (DTE), mercaptopropanoic acid, glutathione, cysteamine, cysteine, tri(carboxyethyl)phosphine (TCEP), and tris (cyanoethyl)phosphine.

In a particular embodiment, the SME is designed based on selection of a small organic molecule having a thiol or protected thiol (disulfide monophore) from a library of such molecules by a Target Biological Molecule (TBM) having a thiol at or near a site of interest. In this case, the method of this invention is a process comprising:
  (i) contacting a TBM containing or modified to contain a thiol, protected thiol or reversible disulfide group at or near a first site of interest on the TBM with a library of small organic molecules, each small organic molecule having a free thiol or a reversible disulfide group (disulfide monophores), under conditions of thiol exchange wherein a library member having affinity for a first site of interest forms a disulfide bond with the TBM;
  (ii) identifying the library member (selected disulfide monophore) from (i); and
  (iii) designing a derivative of the library member in (ii) that is the SME having a first functional group reactive with the thiol on the TBM and having a second functional group which is a thiol, protected thiol or reversible disulfide group.

Just as before, the SME can be designed to contain a first functional group that forms an irreversible or reversible covalent bond with the TBM, and can be used to screen small molecule ligand candidates, in particular libraries of small molecules, as described above, to identify a second ligand.

Thus, in one embodiment, the SME of step (iii) is designed to contain a first functional group that forms an irreversible covalent bond with the thiol on the TBM. Preferred first functional groups of this embodiment are groups capable of undergoing SN2 like additions or forming Michael-type adducts with the thiol. SME's designed in this manner are then contacted with the TBM to form an irreversible TBM-SME complex. This complex is then contacted with second library of small organic molecules, each small organic molecule having a free thiol or a reversible disulfide group, under conditions of thiol exchange wherein the library member having affinity, preferably the highest affinity, for a second site of interest on the TBM (second ligand) forms a disulfide bond with the TBM-SME complex.

In an alternative embodiment, the small molecule extender (SME) of step (iii) is designed to contain a first functional group that forms a first reversible disulfide bond with the thiol on the TBM. SME's designed in this manner are then contacted with the TBM either prior to or simultaneously with contacting the TBM with a second library of small organic molecules, each small organic molecule having a free thiol or a reversible disulfide group, under conditions of thiol exchange under conditions wherein the member of the second library having affinity, preferably the highest affinity, for a second site of interest on the TBM (second ligand) forms a disulfide bond with the TBM-SME complex.

The process may be performed in the presence of a disulfide reducing agent, such as those listed above.

Determining the affinity of a ligand candidate (library member) for a first or second site of interest on a TM or TBM can be carried out by competition between different library members in a pool, or by comparison (i.e. titration) with a reducing agent, such as those listed above.

In a particular embodiment, the invention concerns a process comprising:
  (i) contacting a Target Biological Molecule (TBM) containing or modified to contain a nucleophile at or near a site of interest on the TBM with a small molecule extender having a first functional group reactive with the nucleophile and having a second functional group which is a thiol, protected thiol or reversible disulfide group, thereby forming a TBM-Small Molecule Extender (TBM-SME) complex;
  (ii) contacting the TBM-SME complex with a library of small organic molecules, each small organic molecule (ligand) having a free thiol, protected thiol or a reversible disulfide group, under conditions of thiol exchange wherein a library member having affinity for the site of interest forms a disulfide bond with the TBM-SME complex thereby forming a TBM-SME-ligand complex and
  (iii) determining the ligand from (ii).

In another particular embodiment, the invention concerns a process comprising:
  (i) providing a Target Biological Molecule (TBM) containing or modified to contain a reactive nucleophile near a first site of interest on the TBM;
  (ii) contacting the TBM from (i) with a small molecule extender having a group reactive with the nucleophile on the TBM and having a free thiol or protected thiol;
  (iii) adjusting the conditions to cause a covalent bond to be formed between the nucleophile on the TBM and the group on the small molecule extender thereby forming a covalent complex comprising the TBM and the small molecule extender, the complex displaying a free thiol or protected thiol near a second site of interest on the TBM;
  (iv) contacting the complex from (iii) with a library of small organic molecules, each molecule having a free thiol or exchangeable disulfide linking group, under conditions of thiol exchange wherein the library member having the highest affinity for the second site of interest on the TBM forms a disulfide bond with the complex; and
  (v) identifying the library member from (iv).

In a particular embodiment, the processes of the present invention may be performed with a library in which each member forms a disulfide bond. An example of such a library is one in which each member forms a cysteamine disulfide. When library members form disulfides, a preferred molar ratio of reducing agent to total disulfides is from about 1:100 to about 100:1 and more preferably from about 1:1 to about 50:1.

The tethering process may be performed by contacting members of the disulfide library one at a time with the TBM or in pools of 2 or more. When pools are used it is preferred to use from 5–15 library members per pool.

In all embodiments, the identity of the small molecules that bind to the SME and/or a site of interest on a TM or TBM may be determined, for example, by mass spectrometry (MS), or by means of a detectable tag. When mass spectrometry is used to detect the library member that binds to a TBM and pools are used, it is preferred that each member of the pool differs in molecular weight, preferably by about 10 Daltons. Identification can be performed by measuring the mass of the TBM-library member complex, or by releasing the library member form the complex first or by using a functional assay, e.g. ELISA, enzyme assay etc.

In a different aspect, the invention concerns a molecule comprising a first and/or second ligand identified by any of the methods discussed above. In a particular embodiment, the molecule comprises a first and a second ligand covalently linked to one another. The covalent linkage may be provided by any covalent bond, including but not limited to disulfide bonds.

In a further aspect, the invention concerns methods for synthesizing such molecules. The molecules obtained can, of course, be further modified, for example to impart improved properties, such as solubility, bioavailability, affinity, and half-life. For example, the disulfide bond can be replaced by a linker having greater stability under standard biological conditions. Possible linkers include, without limitation, alkanes, alkenes, aromatics, heteroaromatics, ethers, and the like.

DETAILED DESCRIPTION OF THE INVENTION

1. Definitions

Figure 1:
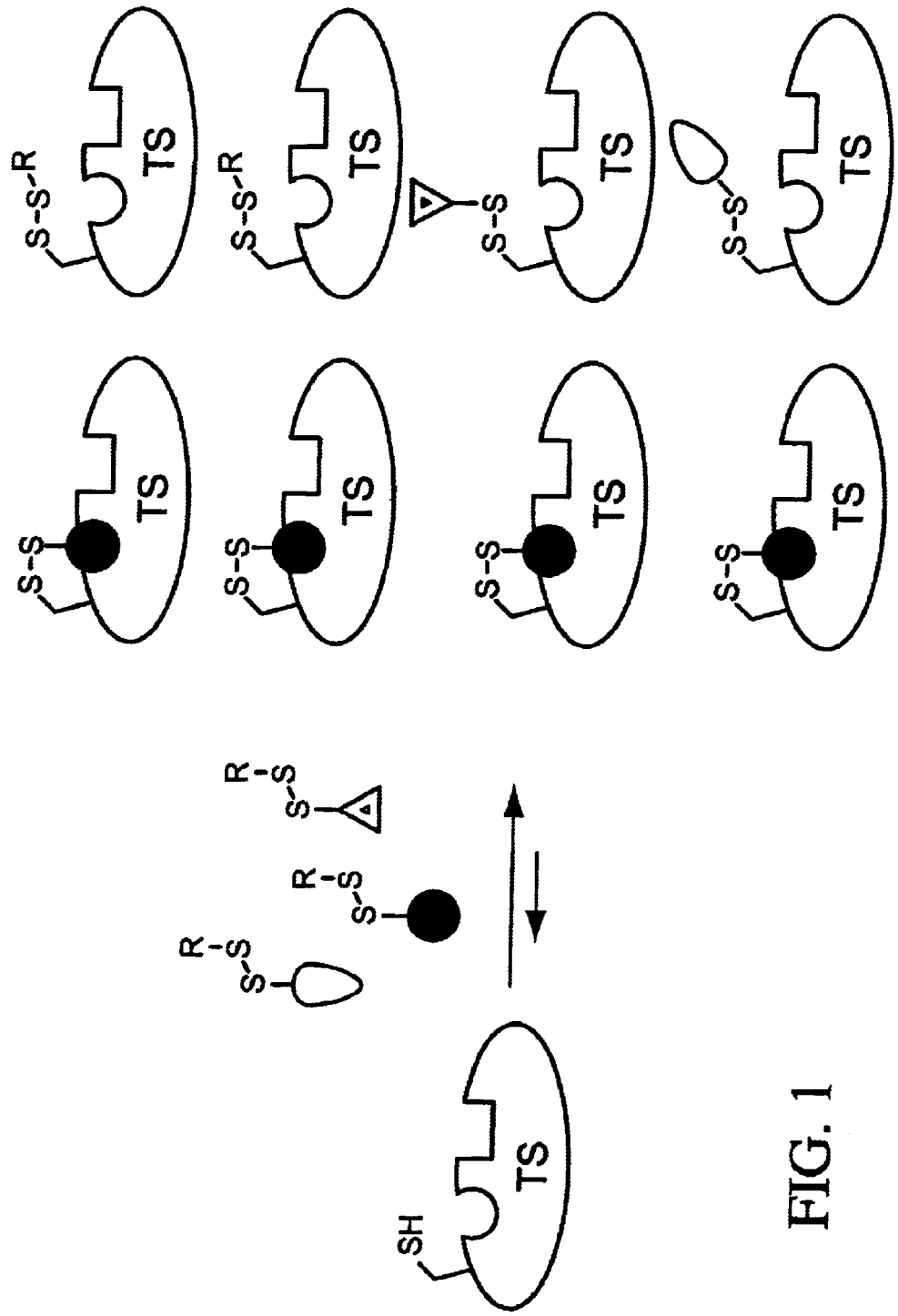
FIG. 1 is a schematic illustration of the basic tethering approach for side-directed ligand discovery. A target molecule, containing or modified to contain a free thiol group (such as a cysteine-containing protein) is equilibrated with a disulfide-containing library in the presence of a reducing agent, such as 2-mercaptoethanol. Most of the library members will have little or no intrinsic affinity for the target molecule, and thus by mass action the equilibrium will lie toward the unmodified target molecule. However, if a library member does show intrinsic affinity for the target molecule, the equilibrium will shift toward the modified target molecule, having attached to it the library member with a disulfide tether.

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

The terms "target," "Target Molecule," and "TM" are used interchangeably and in the broadest sense, and refer to a chemical or biological entity for which a ligand has intrinsic binding affinity. The target can be a molecule, a portion of a molecule, or an aggregate of molecules. The target is capable of reversible attachment to a ligand via a reversible or irreversible covalent bond (tether). Specific examples of target molecules include polypeptides or proteins (e.g., enzymes, including proteases, e.g. cysteine, serine, and aspartyl proteases), receptors, transcription factors, ligands for receptors, growth factors, cytokines, immunoglobulins, nuclear proteins, signal transduction components (e.g., kinases, phosphatases), allosteric enzyme regulators, and the like, polynucleotides, peptides, carbohydrates, glycoproteins, glycolipids, and other macromolecules, such as nucleic acid-protein complexes, chromatin or ribosomes, lipid bilayer-containing structures, such as membranes, or structures derived from membranes, such as vesicles. The definition specifically includes Target Biological Molecules (TBMs) as defined below.

A "Target Biological Molecule" or "TBM" as used herein refers to a single biological molecule or a plurality of biological molecules capable of forming a biologically relevant complex with one another for which a small molecule agonist or antagonist would have therapeutic importance. In a preferred embodiment, the TBM is a polypeptide that comprises two or more amino acids, and which possesses or is capable of being modified to possess a reactive group for binding to members of a library of small organic molecules.

The term "polynucleotide", when used in singular or plural, generally refers to any polyribonucleotide or polydeoxribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes DNAs and RNAs that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

A "ligand" as defined herein is an entity which has an intrinsic binding affinity for the target. The ligand can be a molecule, or a portion of a molecule which binds the target. The ligands are typically small organic molecules which have an intrinsic binding affinity for the target molecule, but may also be other sequence-specific binding molecules, such as peptides (D-, L- or a mixture of D- and L-), peptidomimetics, complex carbohydrates or other oligomers of individual units or monomers which bind specifically to the target. The term "monophore" is used herein to refer to a monomeric unit of a ligand. The term "diaphore" denotes two monophores covalently linked to each other. The term diaphore is used irrespective of whether the unit is covalently bound to the target or existing separately after its release from the target. The term also includes various derivatives and modifications that are introduced in order to enhance binding to the target. The binding affinity of a diaphore that is higher than the product of the affinities of the individual components is referred to as "avidity."

A "site of interest" on a target as used herein is a site to which a specific ligand binds, which may include a specific sequence of monomeric subunits, e.g. amino acid residues, or nucleotides, and may have a three-dimensional structure. Typically, the molecular interactions between the ligand and the site of interest on the target are non-covalent, and include hydrogen bonds, van der Waals interactions and electrostatic interactions. In the case of polypeptide, e.g. protein targets, the site of interest broadly includes the amino acid residues involved in binding of the target to a molecule with which it forms a natural complex in vivo or in vitro.

"Small molecules" are usually less than 10 kDa molecular weight, and include but are not limited to synthetic organic or inorganic compounds, peptides, (poly)nucleotides, (oligo) saccharides and the like. Small molecules specifically include small non-polymeric (e.g. not peptide or polypeptide) organic and inorganic molecules. Many pharmaceutical companies have extensive libraries of such molecules, which can be conveniently screened by using the extended tethering approach of the present invention. Preferred small molecules have molecular weights of less than about 300 DA and more preferably less than about 650 Da.

The term "tether" as used herein refers to a structure which includes a moiety capable of forming a reversible or reversible covalent bond with a target (including Target Biological Molecules as hereinabove defined), near a site of interest.

The phrase "Small Molecule Extender" (SME) as used herein refers to a small organic molecule having a molecular weight of from about 75 to about 1,500 daltons and having a first functional group reactive with a nucleophile or electrophile on a TM and a second functional group reactive with a ligand candidate or members of a library of ligand candidates. Preferably, the first functional group is reactive with a nucleophile on a TBM (capable of forming an irreversible or reversible covalent bond with such nucleophile), and the reactive group at the other end of the SME is a free or protected thiol or a group that is a precursor of a free of protected thiol. In one embodiment, at least a portion of the small molecule extender is capable of forming a noncovalent bond with a first site of interest on the TBM (i.e. has an inherent affinity for such first site of interest). Included within this definition are small organic (including non-polymeric) molecules containing metals such as Cd, Hg and As which may form a bond with the nucleophile e.g. SH of the TBM.

The phrase "reversible covalent bond" as used herein refers to a covalent bond which can be broken, preferably under conditions that do not denature the target. Examples include, without limitation, disulfides, Schiff-bases, thioesters, and the like.

The term "reactive group" with reference to a ligand is used to describe a chemical group or moiety providing a site at which covalent bond with the ligand candidates (e.g. members of a library or small organic compounds) may be formed. Thus, the reactive group is chosen such that it is capable of forming a covalent bond with members of the library against which it is screened.

The term "antagonist" is used in the broadest sense and includes any ligand that partially or fully blocks, inhibits or neutralizes a biological activity exhibited by a target, such as a TBM. In a similar manner, the term "agonist" is used in the broadest sense and includes any ligand that mimics a biological activity exhibited by a target, such as a TBM, for example, by specifically changing the function or expression of such TBM, or the efficiency of signaling through such TBM, thereby altering (increasing or inhibiting) an already existing biological activity or triggering a new biological activity.

The phrases "modified to contain" and "modified to possess" are used interchangeably, and refer to making a mutant, variant or derivative of the target, or the reactive nucleophile or electrophile, including but not limited to chemical modifications. For example, in a protein one can substitute an amino acid residue having a side chain containing a nucleophile or electrophile for a wild-type residue. Another example is the conversion of the thiol group of a cysteine residue to an amine group.

The term "reactive nucleophile" as used herein refers to a nucleophile that is capable of forming a covalent bond with a compatible functional group on another molecule under conditions that do not denature or damage the target, e.g. TBM. The most relevant nucleophiles are thiols, alcohols, activated carbonyls, epoxides, aziridines, aromatic sulfonates, hemiacetals, and amines. Similarly, the term "reactive electrophile" as used herein refers to an electrophile that is capable of forming a covalent bond with a compatible functional group on another molecule, preferably under conditions that do not denature or otherwise damage the target, e.g. TMB. The most relevant electrophiles are imines, carbonyls, epoxides, aziridies, sulfonates, and hemiacetals.

A "first site of interest" on a target, e.g. TBM refers to a site that can be contacted by at least a portion of the SME when it is covalently bound to the reactive nucleophile or electrophile. The first site of interest may, but does not have to possess the ability to form a noncovalent bond with the SME.

The phrases "group reactive with the nucleophile," "nucleophile reactive group," "group reactive with an electrophile," and "electrophile reactive group," as used herein, refer to a functional group on the SME that can form a covalent bond with the nucleophile/electrophile on the TM, e.g. TBM under conditions that do not denature or otherwise damage the TM, e.g. TBM.

The term "protected thiol" as used herein refers to a thiol that has been reacted with a group or molecule to form a covalent bond that renders it less reactive and which may be deprotected to regenerate a free thiol.

The phrase "adjusting the conditions" as used herein refers to subjecting a target, such as a TBM to any individual, combination or series of reaction conditions or reagents necessary to cause a covalent bond to form between the ligand and the target, such as a nucleophile and the group reactive with the nucleophile on the SME, or to break a covalent bond already formed.

The term "covalent complex" as used herein refers to the combination of the SME and the TM, e.g. TBM which is both covalently bonded through the nucleophile/electrophile on the TM, e.g. TBM with the group reactive with the nucleophile/electrophile on the SME, and non-covalently bonded through a portion of the small molecule extender and the first site of interest on the TM, e.g. TBM.

The phrase "exchangeable disulfide linking group" as used herein refers to the library of molecules screened with the covalent complex displaying the thiol-containing small molecule extender, where each member of the library contains a disulfide group that can react with the thiol or protected thiol displayed on the covalent complex to form a new disulfide bond when the reaction conditions are adjusted to favor such thiol exchange.

The phase "highest affinity for the second site of interest" as used herein refers to the molecule having the greater thermodynamic stability toward the second site of interest on the TM, e.g. TBM that is preferentially selected from the library of disulfide-containing library members.

"Functional variants" of a molecule herein are variants having an activity in common with the reference molecule.

"Active" or "activity" means a qualitative biological and/or immunological property.

2. Targets

Targets, such as target biological molecules (TBMs), that find use in the present invention include, without limitation, molecules, portions of molecules and aggregates of molecules to which a ligand candidate may bind, such as polypeptides or proteins (e.g., enzymes, receptors, transcription factors, ligands for receptors, growth factors, immunoglobulins, nuclear proteins, signal transduction components, allosteric enzyme regulators, and the like), polynucleotides, peptides, carbohydrates, glycoproteins, glycolipids, and other macromolecules, such as nucleic acid-protein complexes, chromatin or ribosomes, lipid bilayer-containing structures, such as membranes, or structures derived from membranes, such as vesicles. The target can be obtained in a variety of ways, including isolation and purification from natural source, chemical synthesis, recombinant production and any combination of these and similar methods.

Preferred enzyme target families are cysteine proteases, aspartyl proteases, serine proteases, metalloproteases, kinases, phosphatases, polymerases and integrases. Preferred protein:protein targets are 4-helical cytokines, trimeric cytokines, signaling modules, transcription factors and chemokines.

In a particularly preferred embodiment, the target is a TBM, and even more preferably is a polypeptide, especially a protein. Polypeptides, including proteins, that find use herein as targets for binding ligands, preferably small organic molecule ligands, include virtually any polypeptide (including short polypeptides also referred to as peptides) or protein that comprises two or more binding sites of interest, and which possesses or is capable of being modified to possess a reactive group for binding to a small organic molecule or other ligand (e.g. peptide). Polypeptides of interest may be obtained commercially, recombinantly, by chemical synthesis, by purification from natural source, or otherwise and, for the most parts are proteins, particularly proteins associated with a specific human disease or condition, such as cell surface and soluble receptor proteins, such as lymphocyte cell surface receptors, enzymes, such as proteases (e.g., serine, cysteine, and aspartyl proteases) and thymidylate synthetase, steroid receptors, nuclear proteins, allosteric enzymes, clotting factors, kinases (both serine and threonine) and dephosphorylases (or phophatases, either serine/threonine or protein tyrosine phosphatases, e.g. PTP's, especially PTP1B), bacterial enzymes, fungal enzymes and viral enzymes (especially those associate with HIV, influenza, rhinovirus and RSV), signal transduction molecules, transcription factors, proteins or enzymes associated with DNA and/or RNA synthesis or degradation, immunoglobulins, hormones, receptors for various cytokines including, for example, erythropoietin (EPO), granulocyte colony stimulating (G-CSF) receptor, granulocyte macrophage colony stimulating (GM-CSF) receptor, thrombopoietin (TPO), interleukins, e.g. IL-2, IL-3, IL-4, IL-5, IL-6, IL-10, IL-11, IL-12, growth hormone, prolactin, human placental lactogen (LPL), CNTF, oncostatin, various chemokines and their receptors, such as RANTES MIPβ, IL-8, various ligands and receptors for tyrosine kinase, such as insulin, insulin-like growth factor 1 (IGF-1), epidermal growth factor (EGF), heregulin-α and heregulin-β, vascular endothelial growth factor (VEGF), placental growth factor (PLGF), tissue growth factors (TGF-α and TGF-β), nerve growth factor (NGF), various neurotrophins and their ligands, other hormones and receptors such as, bone morphogenic factors, follicle stimulating hormone (FSH), and luteinizing hormone (LH), trimeric hormones including tissue necrosis factor (TNF) and CD40 ligand, apoptosis factor-1 and -2 (AP-1 and AP-2), p53, bax/bcl2, mdm2, caspases, and proteins and receptors that share 20% or more sequence identity to these.

An important group of human inflammation and immunology targets includes: IgE/IgER, ZAP-70, lck, syk, ITK/BTK, TACE, Cathepsin S and F, CD11a, LFA/ICAM, VLA-4, CD28/B7, CTLA4, TNF alpha and beta, (and the p55 and p75 TNF receptors), CD40L, p38 map kinase, IL-2, IL-4, I1-13, IL-15, Rac 2, PKC theta, IL-8, TAK-1, jnk, IKK2 and IL-18.

Still other important specific targets include: caspases 1, 3, 8 and 9, IL-1/IL-1 receptor, BACE, HIV integrase, PDE IV, Hepatitis C helicase, Hepatitis C protease, rhinovirus protease, tryptase, cPLA (cytosolic Phospholipase A2), CDK4, c-jun kinase, adaptors such as Grb2, GSK-3, AKT, MEKK-1, PAK-1, raf, TRAF's 1–6, Tie2, ErbB 1 and 2, FGF, PDGF, PARP, CD2, C5a receptor, CD4, CD26, CD3, TGF-alpha, NF-KB, IKK beta, STAT 6, Neurokinnin-1, PTP-1B, CD45, Cdc25A, SHIP-2, TC-PTP, PTP-alpha, LAR and human p53, bax/bcl2 and mdm2.

The target, e.g. a TBM of interest will be chosen such that it possesses or is modified to possess a reactive group which is capable of forming a reversible or irreversible covalent bond with a ligand having intrinsic affinity for a site of interest on the target. For example, many targets naturally possess reactive groups (for example, amine, thiol, aldehyde, ketone, hydroxyl groups, and the like) to which ligands, such as members of an organic small molecule library, may covalently bond. For example, polypeptides often have amino acids with chemically reactive side chains (e.g., cysteine, lysine, arginine, and the like). Additionally, synthetic technology presently allows the synthesis of biological target molecules using, for example, automates peptide or nucleic acid synthesizers, which possess chemically reactive groups at predetermined sites of interest. As such, a chemically reactive group may be synthetically introduced into the target, e.g. a TBM, during automated synthesis.

In one particular embodiment, the target comprises at least a first reactive group which, if the target is a polypeptide, may or may not be associated with a cysteine residue of that polypeptide, and preferably is associated with a cysteine residue of the polypeptide, if the tether chosen is a free or protected thiol group (see below). The target preferably contains, or is modified to contain, only a limited number of free or protected thiol groups, preferably not more than about 5 thiol groups, more preferably not more than about 2 thiol groups, more preferably not more than one free thiol group, although polypeptides having more free thiol groups will also find use. The target, such as TBM, of interest may be initially obtained or selected such that it already possesses the desired number of thiol groups, or may be modified to possess the desired number of thiol groups.

When the target is a polynucleotide, a tether can, for example, be attached to the polynucleotide on a base at any exocyclic amine or any vinyl carbon, such as the 5- or 6-position of pyrimidines, 8-or 2-positions of purines, at the 5' or 3' carbons, at the sugar phosphate backbone, or at internucleotide phosphorus atoms. However, a tether can be introduced also at other positions, such as the 5-position of thymidine or uracil. In the case of a double-stranded DNA, for example, a tether can be located in a major or minor groove, close to the site of interest, but not so close as to result in steric hindrance, which might interfere with binding of the ligand to the target at the site of interest.

Those skilled in the art are well aware of various recombinant, chemical, synthesis and/or other techniques that can be routinely employed to modify a target, e.g. a polypeptide of interest such that it possesses a desired number of free thiol groups that are available for covalent binding to a ligand candidate comprising a free thiol group. Such techniques include, for example, site-directed mutagenesis of the nucleic acid sequence encoding the target polypeptide such that it encodes a polypeptide with a different number of cysteine residues. Particularly preferred is site-directed mutagenesis using polymerase chain reaction (PCR) amplification (see, for example, U.S. Pat. No. 4,683,195 issued 28,Jul. 1987; and *Current Protocols In Molecular Biology*, Chapter 15 (Ausubel et al., ed., 1991). Other site-directed mutagenesis techniques are also well known in the art and are described, for example, in the following publications: Ausubel et al., supra, Chapter 8; *Molecular Cloning: A Laboratory Manual.*, 2$^{nd}$ edition (Sambrook et al., 1989); Zoller et al., *Methods Enzymol.* 100:468–500 (1983); Zoller & Smith, *DNA* 3:479–488 (1984); Zoller et al., *Nucl. Acids Res.*, 10:6487 (1987); Brake et al., *Proc. Natl. Acad. Sci. USA* 81:4642–4646 (1984); Botstein et al., *Science* 229:1193 (1985); Kunkel et al., *Methods Enzymol.* 154:367–82 (1987), Adelman et al., *DNA* 2:183 (1983); and Carter et al., *Nucl. Acids Res.*, 13:4331 (1986). Cassette mutagenesis (Wells et al., *Gene,* 34:315 [1985]), and restriction selection mutagenesis (Wells et al., *Philos. Trans. R. Soc. London SerA*, 317:415 [1986]) may also be used.

Amino acid sequence variants with more than one amino acid substitution may be generated in one of several ways. If the amino acids are located close together in the polypeptide chain, they may be mutated simultaneously, using one oligonucleotide that codes for all of the desired amino acid substitutions. If, however, the amino acids are located some distance from one another (e.g. separated by more than ten amino acids), it is more difficult to generate a single oligonucleotide that encodes all of the desired changes. Instead, one of two alternative methods may be employed. In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. The alternative method involves two or more rounds of mutagenesis to produce the desired mutant.

Sources of new reactive groups, e.g. cysteines can be placed anywhere within the target. For example, if a cysteine is introduced onto the surface of the protein in an area known to be important for protein-protein interactions, small molecules can be selected that bind to and block this surface.

The following tables exemplify target biological molecules (TBM's) that can be used in accordance with the present invention.

Tables of Targets

| | Indications |
|---|---|
| Immunology | |
| IL-6 | Inflammation |
| B7/CD28 | Graft rejection |
| CD4 | Immunosuppression |
| CD3 | Immunosuppression |
| CD2 | Renal Transplantation |
| c-maf | Inflammation/Immunosuppression |
| CD11a/LFA1 (ICAM) | Immunosuppression/Inflammation |
| Enzymes | |
| Phospholipase A2 | Inflammation |
| ZAP-70 | Immunosuppression |
| Phophodiesterase IV | Asthma |
| Interleukin converting enzyme (ICE) | Inflammation |
| Inosine monophosphate dehydrogenase | Autoimmune disease |
| Tryptase | Psoriasis/asthma |
| CDK4 | Cancer |
| mTOR | Immunosuppression |
| PARP (Cell death pathway) | Stroke |
| Phosphatases | Cancer |
| Raf | Cancer |
| JNK3 | Neurodegeneration |
| MEK | Cancer |
| GSK-3 | Diabetes |
| FAB1 (Fatty acid biosynthesis) | Bacterial |
| FABH (Fatty acid biosynthesis) | Bacterial |
| BACE | Alzheimer's |
| IkB-ubiquitin Ligase | Inflammation/diabetes |
| Lysophosphatidic acid acetyltransferase | |
| CD26 (dipeptidyl peptidase IV) | |
| Akt | |
| TNF converting enzyme | Inflammation |
| Viral Targets | |
| Rhinovirus protease | Common cold |
| Parainfluenza neuraminidase | Colds/Veterinary uses |
| HIV fusion gp41 | HIV infection/treatment |
| Hepatitis C Helicase | Hepatitis |
| Hepatitis C protease | Hepatitis |
| Protein-Protein Targets | |
| ErbB Receptors | Cancer |
| Neurokinin-1 | Inflammation, Migraine |
| IL-9 | Asthma |
| FGF | Angiogenesis |
| PDGF | Angiogenesis |
| TIE2 | Angiogenesis |
| MFηB Dimerization | Inflammation |
| Tissue Factor/Factor VII | Cardiovascular Disease |
| Selectins | Inflammation |
| TGF-α | Angiogenesis |
| Angiopoietin I | Angiogenesis |

-continued

Tables of Targets

| | Indications |
|---|---|
| APAF-1/Caspase 9 CARD | Stroke |
| Bcl-2 | Cancer |
| 7-Transmembrane | |
| IL-8 | Stroke, inflammation |
| Rantes | Inflammation, Migraine |
| CC Chemokine Receptors | Asthma |
| GPR14/Urotensin | Angiogenesis |
| Orexin/Receptor | Appetite |
| C5a receptor | Sepsis/crohn's disease |
| Histamine H3 receptor | Allergy |
| CCR5 | HIV attachment |

| Target | PDB Codes | Accession No. | Crystal Structure Ref. |
|---|---|---|---|
| BACE | 1FKN | GB AAF13715 | Hong, L. et al., Science. 290(5489):150–3 (2000). |
| Caspase 1 | 1BMQ | SWS P29466 | Okamoto, Y., et al., Chem Pharm Bull (Tokyo), 47(1):11–21 (1999). |
| Caspase 4 | none | SWS P49662 | NA |
| Caspase 5 | none | SWS P51878 | NA |
| Caspase 3 | 1CP3 | SWS P42574 | Mittl, P R, et al., J Biol Chem,272(10):6539–47(1997). |
| Caspase 8 | 1I4E, 1QTN | SWS P08160; GB BAB32555 | Xu, H., et al., Nature, 410(6827):494–7 (2001). |
| Caspase 9 | 3YGS | SWS P55211 | Qin, H., et al., Nature, 399(6736):549–57 (1999). |
| RHV Prot | 1CQQ | SWS P04936 | Matthews, D., et al., 96(20):11000–7 (1999). |
| Cathepsin K | 1MEM | SWS P43235 | McGrath, M E, et al., Nat Struct Biol,4(2):105– (1997). |
| Cathepsin S | 1BXF (model) | SWS P25774 | Fengler, A., et al., Protein Eng,11(11):1007–13(1998). |
| Tryptase | 1A0L | SWS P20231 | Pereira, P. J. et al., Nature, 392(6673):306–11 (1998). |
| HCV Prot | 1A1R, 1DY9 | SWS Q81755 | Di Marco, et al., J Biol Chem. 275(10):7152–7(2000). |
| CD26 | none | SWS P27487 | NA |
| TACE | 1BKC | GB U69612 | Maskos, K., et al., PNAS, 95(7):3408–12 (1998). |
| ZAP-70 | none | SWS P43403 | NA |
| p38 MAP | 1P38 | SWS P47811 | Wang, Z., et al., PNAS, 94(6):2327–32 (1997). |
| CDK-4 | none | SWS Q9XTB6 | NA |
| c-jun kinase | NA | SWS P45983 (C-Jun Kinase-1) | NA |
| | NA | SWS P45984 (C-Jun Kinase-2) | NA |
| | 1JNK | SWS P53779 (C-Jun Kinase-3) | NA |
| GSK-3 | NA | SWS P49840 (GSK-3A) | NA |
| | NA | SWS P49841 (GSK-3B) | NA |
| AKT | none | SWS P31749 | NA |
| MEK | none | SWS Q02750 | NA |
| Raf | none | SWS P04049 | NA |
| TIE-2 | none | SWS Q02763 | NA |
| ILK | none | SWS Q13418 | NA |
| 1kB | NA | SWS O15111 (IKappaBKinase) | NA |
| | NA | SWS O14920 (IKappaBKin-Beta) | NA |
| Jak1 | none | SWS P23458 | NA |
| Jak2 | none | SWS O60674 | NA |
| Jak3 | none | SWS P52333 | NA |
| Tyk2 | none | SWS P29597 | NA |

-continued

| Target | PDB Codes | Accession No. | Crystal Structure Ref. |
|---|---|---|---|
| EGF Kinase | see Vasc. Endo. Growth Factor Receptor (VEGFR) and EGFR both with tyrosine kinase activity(Below): | | |
| VEGFR2/KDR Kinase | NA | SWS P35968 | NA |
| EGFR | NA | SWS P00533 | NA |
| TC-PTP | NA | SWS P17706 | NA: T-cell Protein Tyrosine Phosphatase |
| CDC25A | NA | SWS P30304 | NA |
| CDC25A CDK | NA | GB O14757 (CHKI) | NA |
| CD45 | NA | SWS P08575 | NA |
| PTP alpha | NA | SWS P18433 | NA |
| pol III (PolRIIIA) | NA | SWS O14802 | NA; DNA directed RNA polymerase III |
| mur-D Ligase | NA | GB O14802 (*E. coli*) | NA |
| | NA | SWS P14900 (*E. Coli*) | NA |
| SHP | NA | SWS Q15466 | NA |
| PTP-1B | 1PTP | SWS P00760 | Finer-Moore, J S, et al., Proteins,12(3):203–22(1992). |
| SHIP-2 | none | SWS Q9RIV2 | NA |
| MEKK-1 | NA | SWS Q13233 | NA |
| PAK-1 | NA | SWS Q13153 | NA |
| ICAM-1 | NA | SWS P05362 | Bella, J., et al., Proc Natl Acad Sci USA, 95(8):4140–5 (1998). |
| CD11A/LFA-1 | NA | SWS P20701 | Qu, A., et al., Proc Natl Acad Sci USA, 92(22):10277–81 (1995). |
| TAF1 | UNSURE | UNSURE (see below) | UNSURE |
| | NA | SWS Q99142 (?? Tobacco Prot.) | NA; tobacco Tumor Activating Factor |
| | NA | GB AAB30018 | NA; Tumor-derived Adhesion Factor |
| | NA | GB D45198 | NA; Template Activating Factor |
| HIV-Integrase | 1BL3 (2.0) | SWS P12497 | Maignan, S., et al., J Mol Biol, 282(2):359–68 (1998). |
| | 1EXQ | SWS P04585 | Chen, J. C-H., et al., PNAS USA, 97(15):8233–8 (2000). |
| | NA | SWS O56380 | NA |
| | 1HYZ | SWS O56381; GB AAC37875 | Molteni, V., et al., Acta Crystallogr D Bio Crystallog., 57:536–44 (2001). |
| | 1HYV | GB AAC37875 | Molteni, V., et al., Acta Crystallogr D Biol Crystallogr., 57(Pt 4):536–44 (2001). |
| | NA | SWS O56382 | NA |
| | NA | SWS O56383 | NA |
| | NA | SWS O56384 | NA |
| | NA | SWS O56385 | NA |
| HCV-Helicase | 1N13, 1DY9, others | SWS Q81755 (1DY9) (Integrase) | Di Marco, S., et al., J Biol Chem., 275(10):7152–7 (2000). |
| | 1HE1 | SWS P2664 (Helicase) | Yao, N., et al., Nat Struct Biol, 4(6):463–7 (1997). |
| Infl. Neuraminidase | 1A4G; many | SWS P27907 | Taylor, N., et al., J Med Chem, 41(6):798–807 (1998). |
| PDE-IV | 1FOJ (PDE4B2B) | SWS Q07343 | Xu, R. X., et al., Science, 288(5472):1822–5 (2000). |
| cPLA-2 | 1CJY | SWS P47712 | Dessen, A., et al., Cell., 97(3):349–60 (1999). |
| IL-2 | NA (in-house) | SWS P01585 | NA |
| IL-4 | 1HIK(apo) | SWS P05112 (2.60) | Muller, T., et al., J Mol Biol, 247(2):360–72 (1995). |
| | 1IAR (complex) | SWS P05112 (2.30)** | Hage, T., et al., Cell., 97(2)271–81 (1999). |
| IL-4R | 1IAR | SWS P24394 | Hage, T., et al., Cell., 97(2):271–81 (1999). |

-continued

| Target | PDB Codes | Accession No. | Crystal Structure Ref. |
|---|---|---|---|
| IL-5 | 1HUL | SWS P05113 | Milburn, M. V., et al., Nature, 363(6425):172–6 (1993). |
| IL-6 | 1I1R(viral IL6) | GB AAB62676 (2.6) | Chow, D., et al., Science, 291(5511):2150–5 (2001). |
|  | 1ALU | SWS P05231 (1.9) | Somers, W., et al., EMBO J, 16(5):989–97 (1997). |
| IL-7 | 1IL7 (model) | SWS P13232 | Cosenza, L., et al., Protein Sci., 9(5):916–26 (2000). |
| IL-9 | none | SWS P15248 | NA |
| IL-13 | 1GA3 (NMR) | SWS P35225 | NA |
| TNF | 1TNF | SWS P01375 (TNF-alpha) | Eck, M J, et al., J Biol Chem, 264(29)17595–605(1989). |
| CD-40L | 1ALY | SWS P29965 | Karpusas, M., et al., Structure, 3(12):1426 (1995). |
| OPGL | none | SWS O14788 | NA |
| BAFF | none | SWS Q9Y275 | NA |
| TRAIL | 1DG6 (1.30) | GB AAC50332 | Hymowitz, S. G., et al., Biochemistry, 39(4):633–40 (2000). |
|  | 1DU3 (2.2) | SWS P50591; GB AAC50332 | Cha S S, et al., J Biol Chem, 275(40):31171–7 (2000). |
|  | 1D2Q | GB AAC50332 | Cha and Oh, Immunity, 11(2):253–61 (1999). |
| IL-1 | NA | SWS P01584 (IL-1 B Cytokine) | NA |
| 1L-1R | 1G0Y | SWS P14778 | Vigers, G P A, et al., J Biol Chem., 275(47):26927–33 (2000). |
| IL-8 | 1QE6 | SWS P10145 | Gerber, N., et al., Proteins, 38(4):361–7 (2000). |
| RANTES-R | NA | SWS P32246 | NA |
| RANTES | NA | GB XP 035842 | NA |
|  | NA | SWS P13501 | NA; (T-cell specific RANTES protein) |
| MCP-1 | NA | SWS Q14805 | NA; (Metaphase chromosomal protein) |
| MCP-1 | 1D0K | SWS P13500 | Lubowski, J., et al., Nat Struct Biol., 4(1):64–9 (1997). |
| MCP-3 | NA | SWS P80098 | Nat Struct Biol, 4(1):64–9 (1997). |
| TRAF-A (TRAF-1?) | NA | SWS Q13077 (TRAF-1) | NA |
| TRAF-B (TRAF-2?) | NA | SWS Q12933 (TRAF-2) | NA |
|  | 1D00 (TRAF-2) | GB S56163 (TRAF-2) (2.0) | Ye, H., et al., Mol Cell, 4(3):321–30 (1999). |
| TRAF-C (TRAF-3?) | NA | SWS Q13114 (TRAF-3) | NA |
| TRAF-D (TRAF-4?) | NA | GB XP_008483 (TRAF-4) | NA |
| TRAF-E (TRAF-5?) | NA | GB XP_010656 (TRAF-5) | NA |
| VEGF | 1FLT | SWS P15692 | Wiesmann, C., et al., Cell, 91(5):695–704 (1997). |
| Mineral Corticoid R. | NA | SWS P08235 | NA |
| Estrogen Receptor | 3ERD | SWS P03372 | Shiau, A. K., Barstad, D., Loria, P. M., Cheng, L., Kushner, P. J., Agard, D. A., Greene, G. L., Cell, 95(7):927–37 (1998). |
| Progesterone Rec. | 1A28 | SWS P06401 | Williams, S. P., Sigler, P. B, Nature, 393(6683):392–6 (1998). |
| NF-kappa-B-1 |  | SWS P19838 |  |
| P53 | NA | SWS P04637 | NA |
|  | Y1CQ | GB AAA59989 (2.3) | Kussie, P. H., et al., Science, 74(5289):948–53 (1996). |
| MDM2 | 1YCR | SWS Q00987 | Kussie, P. H., et al., Science, 74(5289):948–53 (1996). |
| STAT6 | NA | SWS P42226 | NA |
| IL4R-alpha | NA | SWS P24394 | NA |
| IL6R-alpha | NA | SWS P08887 | NA |
| IL6R-beta chain | 1BQU | SWS P40189 | Bravo, J., Staunton, D., Heath, J. K., Jones, E. Y., EMBO J, 17(6):1665–74 (1998). |
| IL5R-alpha | NA | SWS Q01344 | NA |
| IL7R | NA | SWS P16871 | NA |
| IL2R-alpha | NA | SWS P01589 | NA |
| IL2R-beta | NA | SWS P14784 | NA |
| HIV GP41 | 1AIK | SWS P19551 | Chan, D. C., Fass, D., Berger, J. M., Kim, P. S., Cell, 89(2):263–73 (1997). |

-continued

| Target | PDB Codes | Accession No. | Crystal Structure Ref. |
|---|---|---|---|
| HIV GP41 | 1AIK | SWS P04582 | Chan, D. C., Fass, D., Berger, J. M., Kim, P. S., Cell, 89(2):263–73 (1997). |
| HIV GP41 | | SWS P03378 | |
| HIV GP41 | | SWS P03375 | |
| HIV GP41 | | SWS P04582 | |
| HIV GP41 | | SWS P12488 | |
| HIV GP41 | | SWS P03377 | |
| HIV GP41 | | SWS P05879 | |
| HIV GP41 | | SWS P04581 | |
| HIV GP41 | | SWS P04578 | |
| HIV GP41 | | SWS P04624 | |
| HIV GP41 | | SWS P12489 | |
| HIV GP41 | | SWS P20871 | |
| HIV GP41 | | SWS P31819 | |
| HIV GP41 | | SWS Q70626 | |
| HIV GP41 | | SWS P04583 | |
| HIV GP41 | | SWS P19551 | |
| HIV GP41 | | SWS P05577 | |
| HIV GP41 | | SWS P18799 | |
| HIV GP41 | | SWS P20888 | |
| HIV GP41 | | SWS P03376 | |
| HIV GP41 | | SWS P04579 | |
| HIV GP41 | | SWS P19550 | |
| HIV GP41 | | SWS P19549 | |
| HIV GP41 | | SWS P05878 | |
| HIV GP41 | | SWS P31872 | |
| HIV GP41 | | SWS P05880 | |
| HIV GP41 | | SWS P35961 | |
| HIV GP41 | | SWS P12487 | |
| HIV GP41 | | SWS P04580 | |
| HIV GP41 | | SWS P05882 | |
| HIV GP41 | | SWS P05881 | |
| HIV GP41 | | SWS P18094 | |
| HIV GP41 | | SWS P24105 | |
| HIV GP41 | | SWS P17755 | |
| HIV GP41 | | SWS P15831 | |
| HIV GP41 | | SWS P18040 | |
| HIV GP41 | | SWS Q74126 | |
| HIV GP41 | | SWS P05883 | |
| HIV GP41 | | SWS P04577 | |
| HIV GP41 | | SWS P32536 | |
| HIV GP41 | | SWS P12449 | |
| HIV GP41 | | SWS P20872 | |
| c-mal | NA | GB NP_071884 | NA; T-cell differentiation protein |
| | NA | GB CAA54102 | NA |
| | NA | GB XP_017128 | NA |
| Mal | NA | SWS P21145 | NA; T-LYMPHOCYTE MATURATION-ASSOCIATED PROTEIN |
| | NA | SWS P01732 | NA; T-LYMPHOCYTE DIFFERENTIATION ANTIGEN T8/CD8(?) |
| Her-1 | NA | SWS P34704 | NA: Cell Signaling in C. elegans Sex Determination |
| Her-2 | NA | SWS P04626 | NA; RECEPTOR PROTEIN-TYROSINE KINASE ERBB-2 |
| E2F-1 | NA | SWS Q01094 | NA |
| E2F-1 | NA | SWS Q14209 | NA |
| E2F-3 | NA | SWS O00716 | NA |
| E2F-4 | NA | SWS Q16254 | NA |
| E2F-5 | NA | SWS Q15329 | NA |
| E2F-6 | NA | SWS O75461 | NA |
| Cyclin A | 1QMZ | SWS P20248 | Brown, N. R., et al., Nat Cell Biol., 1(7):438–43 (1999). |
| mTOR/FRAP | 1NSG | SWS P42345 | Liang, J., et al., Acta Crystall D Biol Crystall, 55 (Pt 4):736–44 (1995). |
| Survivin | 1F3H | SWS O15392 | Verdecia, M. A., et al., Nat Struct Biol., 7(7):602–8 (2000). |
| FGF-1 | 1EV2 | SWS P05230 | Plotnikov, A. N., et al., Cell., 101(4):413–24 (2000). Heparin Binding Growth Factor I) |
| Basic FGF Rec. I | 1FGK | SWS P11362 | Mohammadi, M., et al., Cell, 86(4):577–87 (1996). (Basic FGF Rec. I) |
| FGF-2 | 1CVS | SWS P09038 | Plotkinov, A. N., et al., Cell, 98(5):641–50 (1999). |
| FGF-3 | NA | SWS P11487 | NA |
| FGF-4 | NA | SWS P08620 | NA |

-continued

| Target | PDB Codes | Accession No. | Crystal Structure Ref. |
|---|---|---|---|
| FGF-5 | NA | SWS P12034 | NA |
| FGF-6 | NA | SWS P10767 | NA |
| FGF-7 | NA | SWS P21781 | NA |
| FGF-8 | NA | SWS P55075 | NA |
| FGF-9 | 1IHK | SWS P31371 | Plotnikov, A. N., et al., J Biol Chem., 276(6):4322–9 (2001). |
| PARP | NA | SWS P09874 | NA |
| PDGF-alpha | NA | SWS P04085 | NA |
| PDGF-beta | NA | SWS P01127 | NA |
| C5a receptor | NA | SWS P21730 | NA |
| CCR5 | NA | SWS P51681(CC Chemo R-V) | NA |
| GPR14/Urotensin IIR) | NA | SWS Q9UKP6 | NA |
| Tissue Factor | 2HFT | SWS P13762 | Muller, Y. A., et al., J Mol Biol, 256(1):144–59 (1996). |
| Factor VII | 1JBU | SWS P08709 | Eigenbrot, C., et al., Structure, 9:627 (2001). |
| Histamine H3 rec. | NA | GB CAC39434 | NA |
| Neurokinin-1 | NA | GB SPHUB | NA |
| orexin receptor-1 | NA | SWS O43613 | NA |
| orexin receptor-2 | NA | SWW O43614 | NA |
| CD-3 delta chain | NA | SWS P04234 | NA |
| CD-3 epsilon chain | NA | SWS P07756 | NA |
| CD-3 gamma chain | NA | SWS P09693 | NA |
| CD-3 zeta chain | NA | SWS P20963 | NA |
| CD-4 | 1CDJ | SWS P01730 | Wu, H., et al., Proc Natl Acad Sci USA, 93(26):15030–5 (1996). |
| TGF-alpha | NA | SWS P01135 | NA |
| TGF-beta-1 | NA | SWS P01137 | NA |
| TGF-beta-2 | NA | SWS P08112 | NA |
| TGF-beta-3 | NA | SWS P10600 | NA |
| TGF-beta-4 | NA | SWS O00292 | NA |
| GRB2 | 1GRI (3.1) | SWS P29354 | Maignan S, et al., Science, 268(5208):291–3 (1995). |
| | 1ZFP (1.8) | SWS P29354 | Rahuel, J., et al., J Mol Biol, 279(4):1013–22 (1998). |
| | 1BMB (1.8) | SWS P29354 | Ettmayer, P., et al., J Med Chem, 42(6):971–80 (1999). |
| LCK | 1LKK | SWS P06239;(2nd= P07100) | Tong, L., et al., J Mol Biol, 256(3):601–10 (1996). |
| SRC | 2SRC | SWS P12931 | Xu, W., et al., Mol Cell., 3(5):629–38 (1999). |
| TRAFs? | NA | SWS Q13077 (TRAF-1) | NA |
| | 1CZZ (TRAF-2) | GB S56163 (TRAF-2) (2.7) | Ye, H., et al., Mol Cell, 4(3):321–30 (1999). |
| | 1CZY (TRAF-2) | GB S56153 (TRAF-2) (2.0) | Ye, H., et al., Mol Cell, 4(3):321–30 (1999). |
| | 1D00 (TRAF-2) | GB S56163 (TRAF-2) (2.0) | Ye, H., et al., Mol Cell, 4(3):321–30 (1999). |
| | NA | SWS Q12933 (TRAF-2) | NA |
| | 1FLK (TRAF-3) | GB Q13114 (TRAF-3) (2.8) | Ni, C.-Z., et al., Proc Natl Acad Sci USA., 97(19):10395–9 (2000). |
| BAX/BCL-2 | NA | SWS Q07812 (BAX alpha) | NA |
| | NA | SWS Q07814 (BAX beta) | NA |
| | NA | SWS Q07815 (BAX gamma) | NA |
| | NA | SWS P55269 (BAX delta) | NA |
| | NA | SWS P10415 (BCL-2) | NA |
| IgE | 1F6A (3.5) | SWS P01854 (IgE chain C) | Garman, S. C., et al., T. S., Nature., 406(6793):259–66 (2000). |
| IgER | NA | SWS P06734 (IgE Fc | NA |

-continued

| Target | PDB Codes | Accession No. | Crystal Structure Ref. |
|---|---|---|---|
| | 1F6A (3.5) | Receptor)<br>SWS P12319<br>(IgE Fc Rec. alpha) | Garman, S. C., et al., T. S., Nature., 406(6793):259–66 (2000). |
| | 1F2Q (2.4) | SWS P12319<br>(IgE Fc Rec. alpha) | Garman, S. C., Kinet, J. P., Jardetzky, T. S., Cell, 95(7):951–61 (1998). |
| | NA | SWS Q01362<br>(IgE FcRec. Beta) | NA |
| | NA | SWS P30273<br>(IgE FcRec. Gama) | NA |
| Rhinovirus Protease | NA | SWS P03303<br>(HRV-14 polyprot.) | NA |
| | NA | SWS P12916<br>(HRV-1B) | NA |
| | 1CQQ | SWS P04936<br>(HRV-2) (1.85) | Matthews, D., et al., Proc Natl Acad Sci USA, 96(20):11000–7 (1999). |
| | NA | SWS P07210<br>(HRV-89) | NA |
| | 1C8M | SWS Q82122 | Chakravarty, S., et al., to be published |
| B7/CD28LG/CD80 | 1DR9 | SWS P33681 | Ikemizu, S., et al., Immunity. 2000 Jan; 12(1):51–60. |
| CD28 | NA | SWS P10747 | NA |
| APAF1 | NA | SWS O14727 | NA |

3. Site(s) of Interest

Broadly, the "site of interest" on a particular target, such as a Target Biological Molecule (TBM), is defined by the residues that are involved in binding of the target to a molecule with which it forms a natural complex in vitro or in vivo. If the target is a peptide, polypeptide, or protein, the site of interest is defined by the amino acid residues that participate in binding to (usually by non-covalent association) to a ligand of the target.

When, for example, the target biological molecule is a protein that exerts its biological effect through binding to another protein, such as with hormones, cytokines or other proteins involved in signaling, it may form a natural complex in vivo with one or more other proteins. In this case, the site of interest is defined as the critical contact residues involved in a particular protein:protein binding interface. Critical contact residues are defined as those amino acids on protein A that make direct contact with amino acids on protein B, and when mutated to alanine decrease the binding affinity by at least 10 fold and preferably at least 20 fold, as measured with a direct binding or competition assay (e.g. ELISA or RIA). See (A Hot Spot of Binding Energy in a Hormone-Receptor Interface by Clackston and Wells Science 267:383–386 (1995) and Cunningham and Wells J. Mol. Biol, 234:554–563 (1993)). Also included in the definition of a site of interest are amino acid residues from protein B that are within about 4 angstroms of the critical contact residues identified in protein A.

Scanning amino acid analysis can be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant (Cunningham and Wells, Science, 244: 1081–1085 (1989)). Alanine is also typically preferred because it is the most common amino acid. Further, it is frequently found in both buried and exposed positions (Creighton, The Proteins, (W.H. Freeman & Co., N.Y.); Chothia, J. Mol. Biol., 150:1 (1976)). If alanine substitution does not yield adequate amounts of variant, an isoteric amino acid can be used.

When the target biological molecule is an enzyme, the site of interest can include amino acids that make contact with, or lie within, about 4 angstroms of a bound substrate, inhibitor, activator, cofactor or allosteric modulator of the enzyme. By way of illustration, when the enzyme is a protease, the site of interest would include the substrate binding channel from P4 to P4', residues involved in catalytic function (e.g. the catalytic triad) and any cofactor (e.g. Zn) binding site. For protein kinases, the site of interest would include the substrate-binding channel (as above) in addition to the ATP binding site. For dehydrogenases, the site of interest would include the substrate binding region as well as the site occupied by NAD/NADH. In hydrolases such as PDE4, the site of interest would include all residues contacting the cAMP substrate, as well as residues involved in binding the catalytic divalent cations (Xu, R. X. et al. Science 288:1822–1825 (2000)).

For an allosterically regulated enzyme, such as glycogen phosphorylase B, the site of interest includes all residues in the substrate binding region, residues in contact with the natural allosteric inhibitor glucose-6-phosphate, and residues in novel allosteric sites such as those identified in binding other inhibitors such as CP320626 (Oikonomakos NG, et al. Structure Fold Des 8:575–584 (2000)).

The TBM's either contain, or are modified to contain, a reactive residue at or near a site of interest. Preferably, the TBM's contain or are modified to contain a thiol-containing amino acid residue at or near a site of interest. In this case, after a TBM is selected, the site of interest is calculated.

Once the site of interest is known, a process of determining which amino acid residue within, or near, the site of interest to modify is undertaken. For example, one preferred modification results in substituting a cysteine residue for another amino acid residue located near the site of interest.

The choice of which residue within, or near, the site of interest to modify is determined based on the following selection criteria. First, a three dimensional description of the TBM is obtained from one of several well-known sources. For example, the tertiary structure of many TBMs has been determined through x-ray crystallography experiments. These x-ray structures are available from a wide variety of sources, such as the Protein Databank (PDB) which can be found on the Internet at http://www.rcsb.org. Tertiary structures can also be found in the Protein Structure Database (PSdb) which is located at the Pittsburg Supercomputer Center at http://www.psc.com.

In addition, the tertiary structure of many proteins, and protein complexes, has been determined through computer-based modeling approaches. Thus, models of protein three-dimensional conformations are now widely available.

Figure 2:
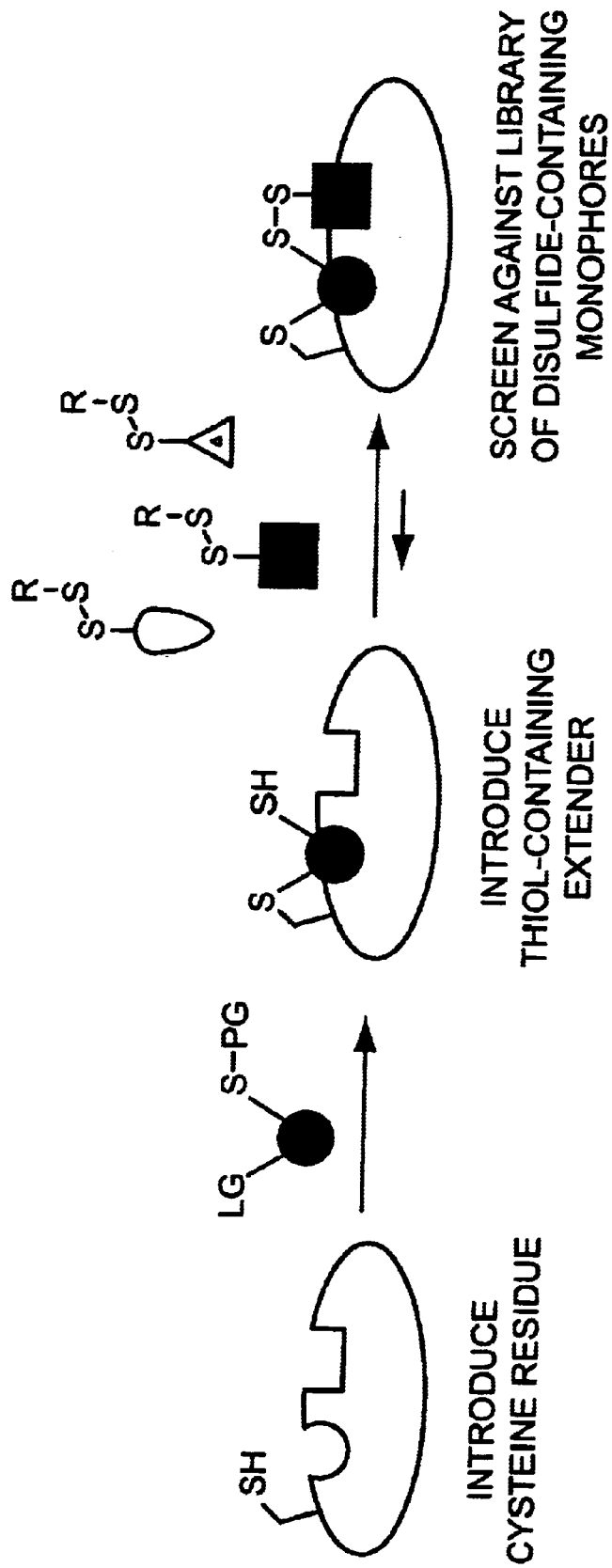
FIG. 2 is a schematic illustration of the static extended tethering approach. In the first step, a target molecule containing or modified to contain a free thiol group (such as a cysteine-containing protein) is modified by a thiol-containing extender, comprising a reactive group capable of forming an irreversible covalent bond with the thiol group on the target molecule, a portion having intrinsic affinity for the target molecule, and a thiol group. The complex formed between the target molecule and the thiol-containing extender is then used to screen a library of disulfide-containing monophores to identify a library member that has the highest intrinsic binding affinity for a second binding site on the target molecule. LG=leaving group; PG=protecting group; R=reactive group.

Once the three dimensional structure of the TBM is known, a measurement is made based on a structural model of the wild type, or a variant form, of the target biological molecule from any atom of an amino acid within the site of interest across the surface of the protein for a distance of approximately 10 angstroms. Variant, which have been modified to contain the desired reactive groups (e.g. thiol groups, or thiol-containing residues) are based on the identification of one or more wild-type amino acid(s) on the surface of the target biological molecule that fall within that approximate 10-angstrom radius from the site of interest. For the purposes of this measurement, any amino acid having at least one atom falling within the about 10 angstrom radius from any atom of an amino acid within the site of interest is a potential residue to be modified to a thiol containing residue.

Preferred residues for modification are those that are solvent-accessible. Solvent accessibility may be calculated from structural models using standard numeric (Lee, B. & Richards, F. M. *J. Mol. Biol* 55:379–400 (1971); Shrake, A. & Rupley, J. A. *J. Mol. Biol.* 79:351–371 (1973)) or analytical (Connolly, M. L. *Science* 221:709–713 (1983); Richmond, T. J. *J. Mol. Biol.* 178:63–89 (1984)) methods. For example, a potential cysteine variant is considered solvent-accessible if the combined surface area of the carbon-beta (CB), or sulfur-gamma (SG) is greater than 21 $Å^2$ when calculated by the method of Lee and Richards (Lee, B. & Richards, F. M. *J. Mol. Biol* 55:379–400 (1971)). This value represents approximately 33% of the theoretical surface area accessible to a cysteine side-chain as described by Creamer et al. (Creamer, T. P. et al. *Biochemistry* 34:16245–16250 (1995)).

It is also preferred that the residue to be mutated to cysteine, or another thiol-containing amino acid residue, not participate in hydrogen-bonding with backbone atoms or, that at most, it interacts with the backbone through only one hydrogen bond. Wild-type residues where the side-chain participates in multiple (>1) hydrogen bonds with other side-chains are also less preferred. Variants for which all standard rotamers (chil angle of −60°, 120°, or 180°) can introduce unfavorable steric contacts with the N, CA, C, O, or CB atoms of any other residue are also less preferred. Unfavorable contacts are defined as interatomic distances that are less than 80% of the sum of the van der Waals radii of the participating atoms.

Wild-type residues that fall within highly flexible regions of the protein are less preferred. Within structures derived from x-ray data, highly flexible regions can be defined as segments where the backbone atoms possess weak electron density or high temperature factors (>4 standard deviations above the mean temperature factor for the structure). Within structures derived from NMR data, highly flexible regions can be defined as segments possessing <5 experimental restraints (derived from distance, dihedral coupling, and H-bonding data) per residue, or regions displaying a high variability (>2.0 $A^2$ RMS deviation) among the models in the ensemble. Additionally, residues found on convex "ridge" regions adjacent to concave surfaces are more preferred while those within concave regions are less preferred cysteine residues to be modified. Convexity and concavity can be calculated based on surface vectors (Duncan, B. S. & Olson, A. J. *Biopolymers* 33:219–229 (1993)) or by determining the accessibility of water probes placed along the molecular surface (Nicholls, A. et al. *Proteins* 11:281–296 (1991); Brady, G. P., Jr. & Stouten, P. F. *J. Comput. Aided Mol. Des.* 14:383–401 (2000)). Residues possessing a backbone conformation that is nominally forbidden for L-amino acids (Ramachandran, G. N. et al. *J. Mol. Biol.* 7:95–99 (1963); Ramachandran, G. N. & Sasisekharahn, V. *Adv. Prot. Chem.* 23:283–437 (1968)) are less preferred targets for modification to a cysteine. Forbidden conformations commonly feature a positive value of the phi angle.

Other preferred variants are those which, when mutated to cysteine and linked via a disulfide bond to an alkyl tether, would possess a conformation that directs the atoms of that tether towards the site of interest. Two general procedures can be used to identify these preferred variants. In the first procedure, a search is made of unique structures (Hobohm, U. et al. *Protein Science* 1:409–417 (1992)) in the Protein Databank (Berman, H. M. et al. *Nucleic Acids Research* 28:235–242 (2000)) to identify structural fragments containing a disulfide-bonded cysteine at position j in which the backbone atoms of residues j−1,j, and j+1 of the fragment can be superimposed on the backbone atoms of residues i−1, i, and i+1 of the target molecule with an RMSD of less than 0.75 $A^2$. If fragments are identified that place the CB atom of the residue disulfide-bonded to the cysteine at position j closer to any atom of the site of interest than the CB atom of residue i (when mutated to cysteine), position i is considered preferred. In an alternative procedure, the residue at position i is computationally "mutated" to a cysteine and capped with an S-Methyl group via a disulfide bond.

Further details of identifying site(s) of interest on the targets of the invention are provided in co-pending application Ser. No. 60/310,725, filed on Aug. 7, 2001, the entire disclosure of which is hereby expressly incorporated by reference.

4. Small Molecule Extender (SME)

(A) Static SME

In one embodiment of the invention the SME forms a "static" or irreversible covalent bond through the nucleophile or electrophile, preferably nucleophile, on the TBM, thereby forming an irreversible TBM-SME complex. This method is illustrated in FIG. 2. Optionally the SME also forms a non-covalent bond with a first site of interest on the TBM. Additionally the SME contains a second functional group capable of forming a reversible bond with a library member of a library of small organic molecules, each molecule having a functional group capable of forming a reversible bond with the second functional group of the SME. The TBM-SME complex and library are subjected to conditions wherein the library member having affinity, preferably the highest affinity, for the second site of interest on the TBM forms a reversible bond with the TBM-SME complex.

Preferred TBM's are proteins and the preferred nucleophiles on the TBM's suitable for forming an irreversible TBM-SME complex include —SH, —OH, —NH$_2$ and —COOH usually arising from side chains of cys, ser or thr, lys and asp or glu respectively. TBM's may be modified (e.g. mutants or derivatives) to contain these nucleophiles or may contain them naturally. For example, cysteine proteases (e.g. Caspases, especially 1, 3, 8 and 9; Cathesepins, especially S and K etc.) and phosphatases (e.g. PTPα, PTP1B, LAR, SHP1,2, PTPβ and CD45) are examples of suitable proteins containing naturally occurring cysteine thiol nucleophiles. Derivatizing such TBM's with a SME to produce a static TBM-SME complex and its reaction with a library member is illustrated below.

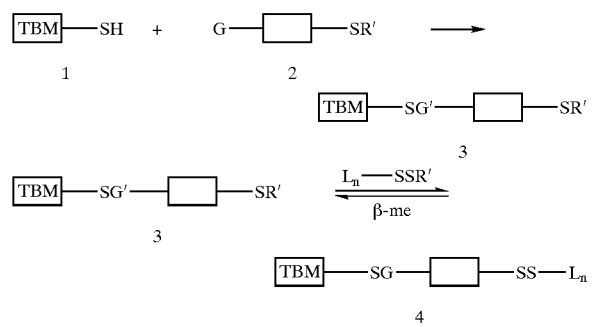

Here, the nucleophile on the TBM is the sulfur of a thiol, usually a cysteine, which is reacted with 2, a SME containing a substituent G capable of forming an irreversible (under conditions that do not denature the target) covalent bond and a free thiol, protected thiol or derivatized thiol SR'. Preferably G is a group capable of undergoing SN2-like attack by the thiol or forming a Michael-type adduct with the thiol to produce the irreversible reaction product 3 of that attack having a new covalent linkage —SG'—. The following are representative examples of G groups capable of undergoing SN2-like or Michael-type addition.

1) α-halo acids: F, Cl and Br substituted α to a COOH, PO$_3$H$_2$ or P(OR)O$_2$H acid that is part of the SME can form a thioether with the thiol of the TBM. Simple examples of such a G-SME-SR' are;

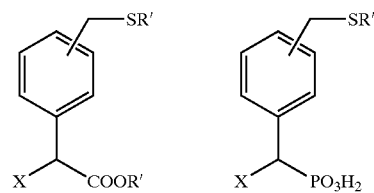

where X is the halogen and R' is H, SCH$_3$, S(CH$_2$)$_n$A, where A is OH, COOH, SO$_3$H, CONH$_2$ or NH$_2$ and n is 2 or 3.

2) Fluorophos(phon)ates: These can be Sarin-like compounds which react readily with both SH and OH nucleophiles. For example, cys 215 of PTP1B can be reacted with a simple G-SME-SR' represented by the following:

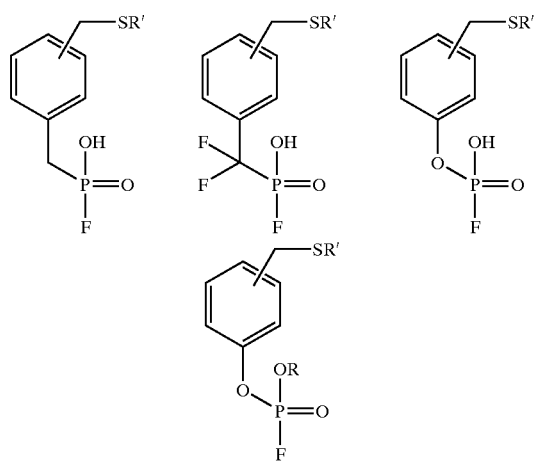

Here the phenyl ring represents a simplified SME, R is a substituted or unsubstituted loweralkyl and R' is as defined above. These compounds form thiophos(phon)ate SME's with the thiol nucleophile. These compounds also are capable of forming static TBM-SME's with naturally occurring —OH from serine or threonine phosphatases or β-lactamases.

3) Epoxides, aziridines and thiiranes: SME's containing these reactive functional groups are capable of undergoing SN2 ring opening reactions with —SH, —OH and —COOH nucleophiles. Preferred examples of the latter are aspartyl proteases like β-secretase (BASE). Preferred generic examples of epoxides, aziridines and thiiranes are shown below.

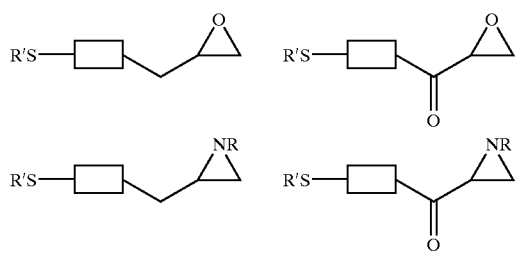

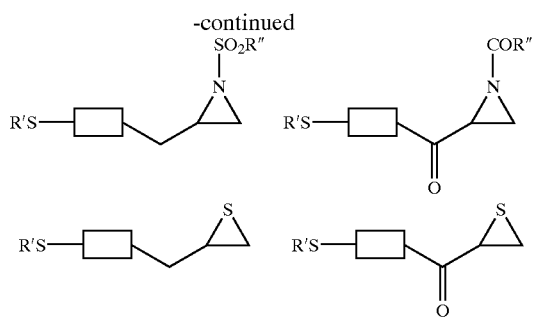

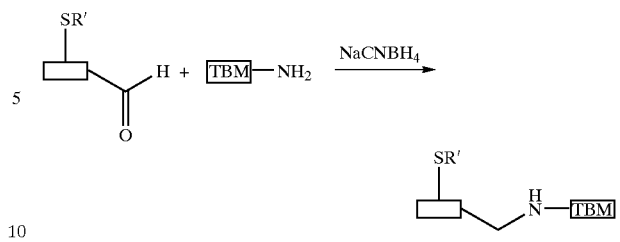

Here, R' is as defined above, R is usually H or lower alkyl and R" is lower alkyl, lower alkoxy, OH, NH$_2$ or SR'. In the case of thiiranes the group SR' is optionally present because upon nucleophilic attack and ring opening a free thiol is produced which may be used in the subsequent extended tethering reaction.

4) Halo-methyl ketones/amides: These compounds have the form —(C═O)—CH$_2$—X. Where X may be a large number of good leaving groups like halogens, N$_2$, O—R (Where R may be substituted or unsubstituted heteroaryl, Aryl, alkyl, —(P═O)Ar$_2$, —N—O—(C═O) aryl/alkyl, —(C═O) aryl/alkyl/alkylaryl and the like), S-Aryl, S-heteroaryl and vinyl sulfones.

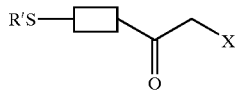

Fluromethylketones are simple examples of this class of activated ketones which result in the formation of a thioether when reacted with a thiol containing protein. Other well known examples include acyloxymethyl ketones like benzoyloxymethyl ketone, aminomethyl ketones like phenylmethylaminomethyl ketone and sulfonylaminomethyl ketones. These and other types of suitable compounds are reviewed in J. Med. Chem. 43(18) p3351–71, Sep. 7, 2000.

5) Electrophilic aromatic systems: Examples of these include 7-halo-2,1,3-benzoxadiazoles and ortho/para nitro substituted halobenzenes.

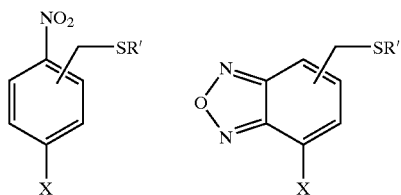

Compounds of this type form arylalkylthioethers with TBM's containing a thiol.

6) Other suitable SN2 like reactions suitable for formation of static covalent bonds with TBM nucleophiles include formation of a Schiff base between an aldehyde and the amine group of lysine an enzymes like DNA repair proteins followed by reduction with for example NaCNBH$_4$.

7) Michael-type additions: Compounds of the form —RC═CR-Q, or —C≡C-Q where Q is C(═O)H, C(═O)R (including quinines), COOR, C(═O)NH$_2$, C(═O)NHR, CN, NO$_2$, SOR, SO$_2$R, where each R is independently substituted or unsubstituted alkyl, aryl, hydrogen, halogen or another Q can form Michael adducts with SR (where R is H, glutathione or S-loweralkyl substituted with NH$_2$ or OH), OH and NH$_2$ on the TBM.

8) Boronic acids: These compounds can be used to label ser or thr hydroxyls to form TBM-SME complexes of the form shown below:

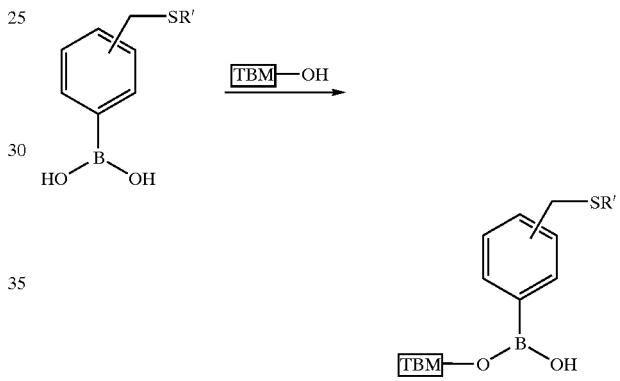

where R' is as defined above

In each of the foregoing cases a "static" or irreversible covalent bond is formed through the nucleophile on the TBM producing an irreversible TBM-SME complex containing a thiol or protected thiol. These complexes are then exposed to a library of thiol or disulfide containing organic compounds in the presence of a reducing agent (e.g. mercaptoethanol) for selection of a small molecule ligand capable of binding a second binding site on the TBM.

As noted above, in this static approach, the SME may, but does not have to, include a portion that has binding affinity (i.e. is capable of bonding to) a first site of interest on the TBM. Even if the SME does not include such portion, it must be of appropriate length and flexibility to ensure that the ligand candidates have free access to the second site of interest on the target.

(B) Dynamic SME

In another embodiment of the invention the SME is a double reversible covalent bond SME ("double disulfide" extender), that is, this SME is bifunctional and contains two functional groups (usually disulfide) capable of forming reversible covalent bonds. This SME forms a "dynamic" or first reversible covalent bond through a first functional group on the SME with the nucleophile on the TBM, thereby forming a reversible TBM-SME complex (7 below). Optionally the SME also forms a non-covalent bond with a first site of interest on the TBM (the portion of the SME that forms a non-covalent bond with the TBM is referred to herein as SME'). Additionally the SME contains or is modified to contain a second functional group capable of forming a second reversible bond with a library member of a second library of small organic molecules, each molecule having a functional group capable of forming a reversible bond with the first or second functional group of the SME. The TBM-SME complex and the second library are subjected to conditions wherein the library member having the highest affinity for a second site of interest on the TBM forms a reversible bond with the TBM-SME complex (8 below). Preferably the covalent bonds are disulfides, which may be reversible in the presence of a reducing agent.

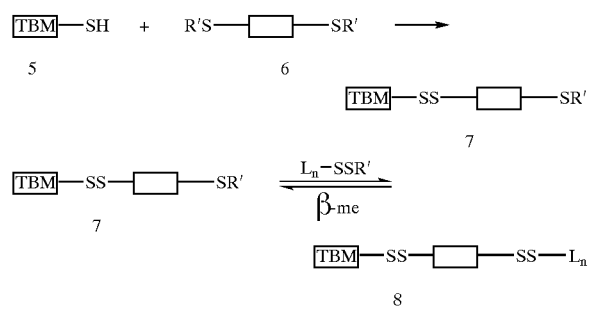

Figure 3:
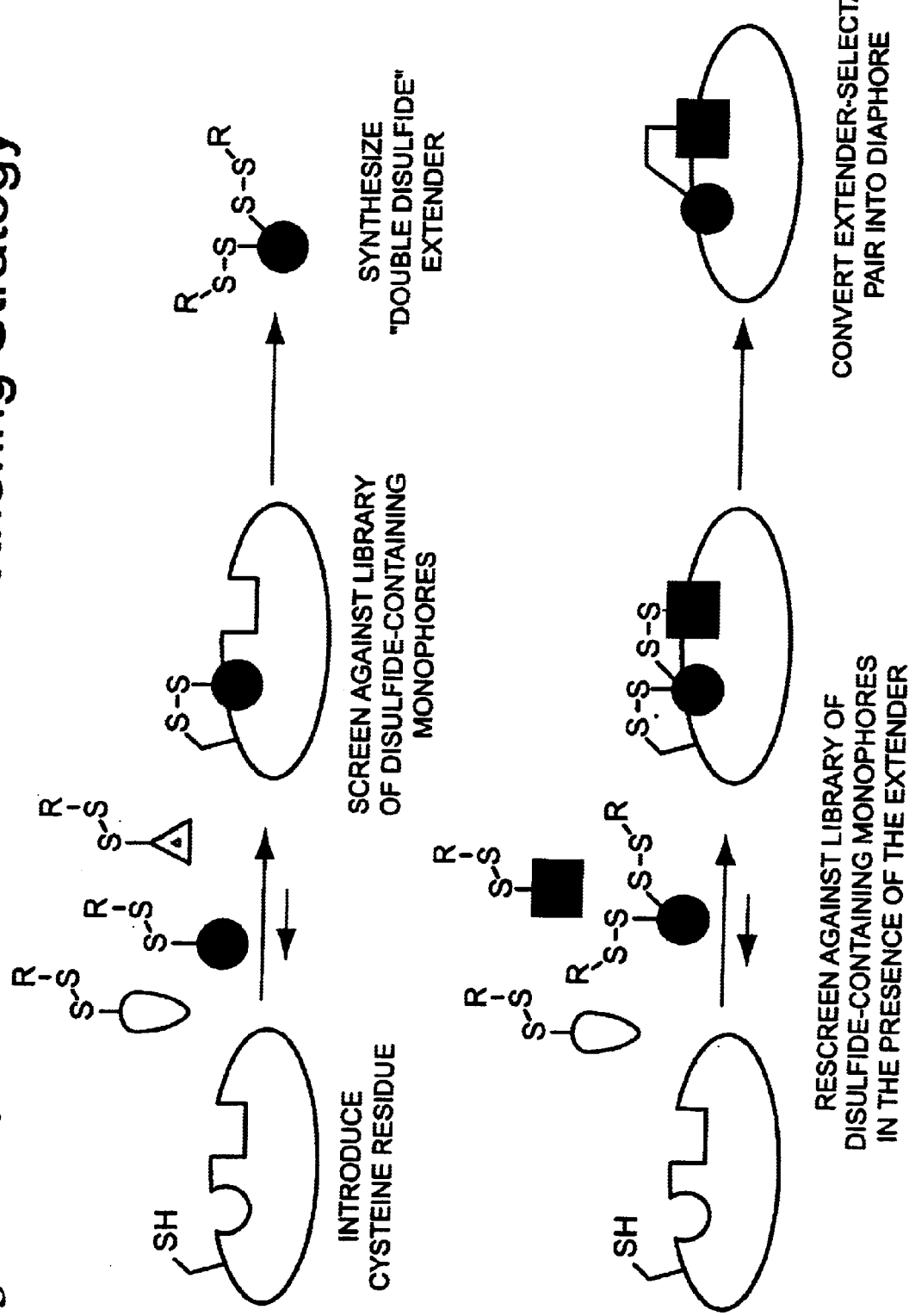
FIG. 3 illustrates the dynamic extended tethering strategy, where the extender is bifunctional and contains two functional groups (usually disulfide), each capable of forming reversible covalent bonds. R=reactive group.

The dynamic extended tethering process is illustrated in FIG. 3 where a TMB containing or modified to contain a thiol or protected thiol is incubated with a first library of small organic molecules containing a thiol or protected thiol (a disulfide-containing monophore) under conditions, such as with a reducing agent, wherein at least one member of the library forms a disulfide bond linking the selected library member with the TBM. Optionally this process is repeated with a library of TBM's differing from one another by the location of the thiol or protected thiol, i.e. different cysteine mutants of the same protein. Preferably each member of the small molecule library differs in molecular weight from each of the other library members. Preferably the small molecule library contains from 1–100 members, more preferable from 5–15 and most preferably about 10 members. Optionally the selected small molecule library member (selected monophore) also forms a noncovalent bond with a first site of interest on the TBM. The selected monophore, or a derivative thereof, is then modified to contain a second thiol or protected thiol thereby forming a "double disulfide" extender. This synthetic double disulfide extender is then incubated with the TBM in the presence of a second library of small organic molecules containing a thiol or protected thiol (the library may be the same or different from the first library) under conditions, such as with a reducing agent like mercaptoethanol, wherein at least one member of the second library forms a disulfide bond linking the selected library member with the TBM through the double disulfide extender as shown in 8 above. Optionally thereafter a diaphore is synthesized based on the two selected library members (monophores).

Two basic strategies exist for synthesizing a "double disulfide" extender. In the first, synthesis of the dynamic extender proceeds generically, that is by modification of the monophore linker without any modification of the portion of the monophore that forms a non-covalent bond with the TBM. By way of illustration, the extender usually arises from the screening of a disulfide monophore library as shown in FIG. 3. A typical monophore selected from the library or pool will contain a linker of 2 or 3 methylene units between the disulfide that links the monophore to the TBM cysteine and the portion of the monophore that binds non-covalently to the first site of interest on the TBM. This monophore linker can be derivatized as shown below to produce a double disulfide extender in which the "R" or variable group of the monophore remains invariant and becomes the portion of the extender (SME') that binds non-covalently with the first site of interest on the TBM.

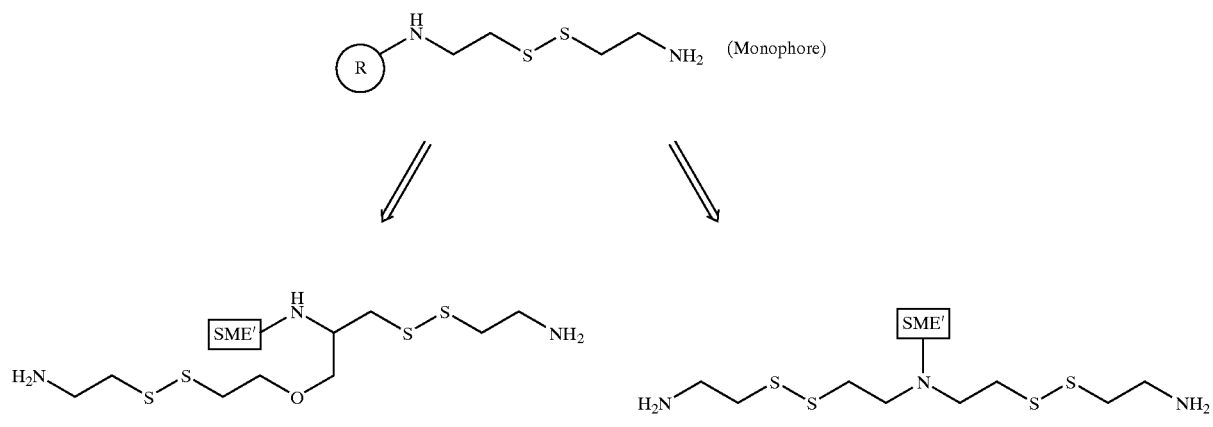

Here the monophore is derivatized either at the methylene nearest the cysteamine nitrogen to produce dynamic double disulfide extender 1 or at the cysteamine nitrogen itself to produce the symmetrical dynamic double disulfide extender 2.

Alternatively, when the monophore is a 3-mercaptopropionic acid derivative the alpha carbon can be derivatized to produce a generic dynamic double disulfide extender of the form shown in 3 below.

linked compound having a higher affinity for the TBM than either the SME or selected monophore alone.

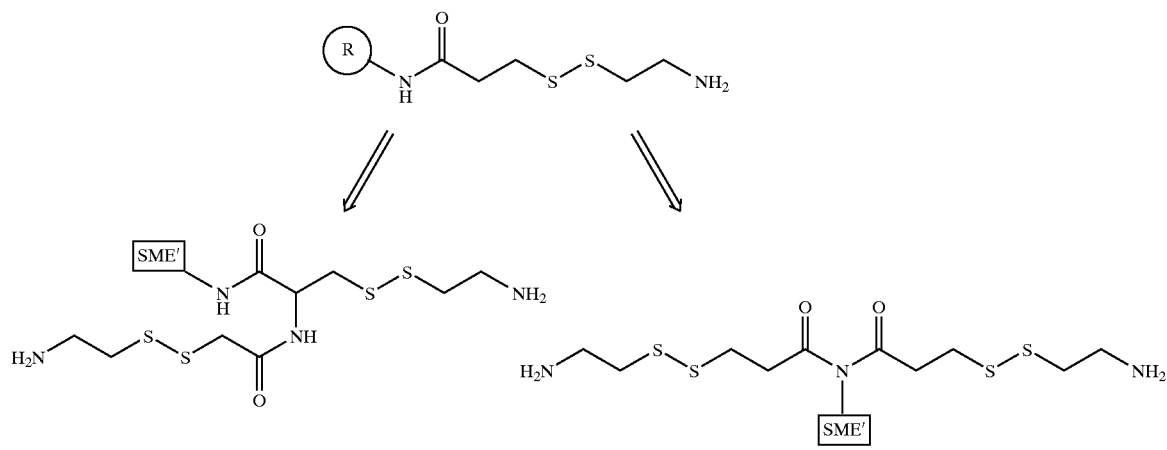

Dynamic Double Disulfide Extender 3

Dynamic Double Disulfide Extender 4

Optionally the amide nitrogen may be derivatized with an acyl or sulfonyl to produce an extender of the form shown in 4 above.

A second strategy involves derivatizing the portion of the monophore that binds non-covalently to the first site of interest on the TBM. The derivatization is preferably carried out at a site that minimally alters the binding of the monophore to the first site of interest as illustrated below.

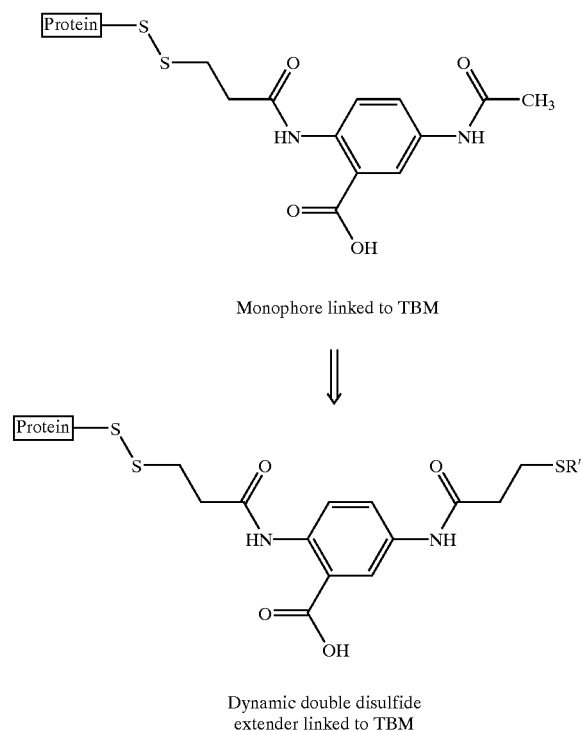

Monophore linked to TBM

Dynamic double disulfide extender linked to TBM

Here the dynamic tether is shown bound to the TBM thiol forming the TBM-SME complex, where R' is the cysteamine radical. This complex can then be contacted with a disulfide monophore or library of disulfide monophores to obtain a A second example of a SME designed form a disulfide monophore that binds to the TBM is shown below. This dynamic SME can be contacted with the TBM in the presence of one or more disulfide monophores to form a covalent TBM-SME-monophore complex where the SME has an affinity for the first site of interest and the monophore has an affinity for the second site of interest on the TBM.

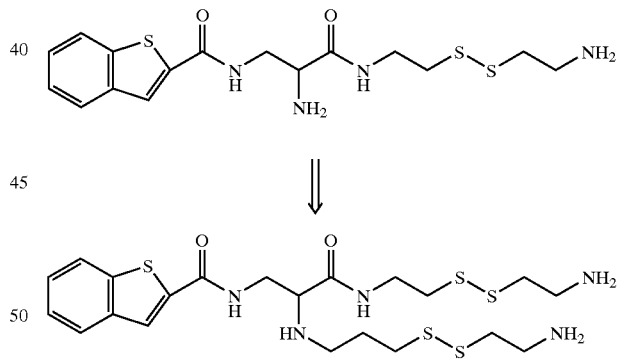

Detection and identification of the structure of the TBM-SME-monophore complex can be carried out by mass spectrometry or inhibition in a functional assay (e.g. ELISA, enzyme assay etc.).

SME's are often customized for a particular TBM or family of TBM's. For example quinazoline derivatives are capable of forming static or dynamic extenders with the EGF receptor or an "RD" kinase. In the case of the EGF receptor, cys 773 is a suitable nucleophile for either a static or dynamic quinazoline extender as shown below;

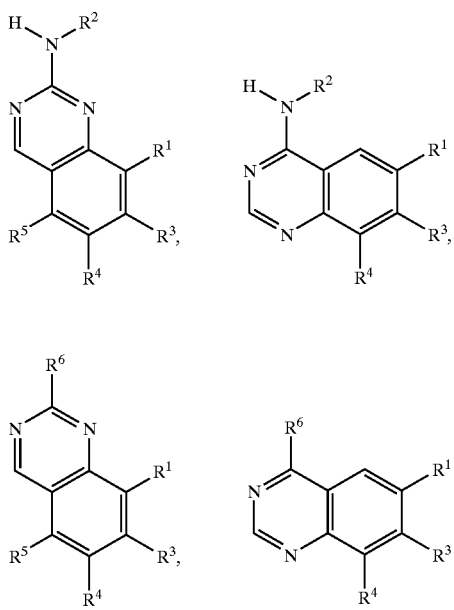

where R¹ is linked to cys 773 through a Michael acceptor or disulfide,

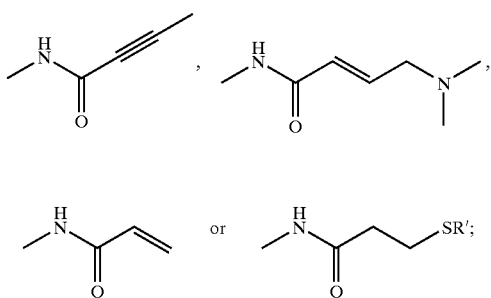

R² is —(CH$_2$)$_n$—SR' and —C(=O)—(CH$_2$)$_n$—SR';
R³, R⁴ and R⁵ are —O—(CH$_2$)$_n$—SR' and —(CH$_2$)$_n$—SR';
R⁶ are; —(CH$_2$)$_n$—SR'; where n is 1, 2, or 3 and
R' is H, a disulfide or a thiol protecting group.

Phosphotyrosine (P-tyr), phosphoserine (P-ser) and phoshpothreonine (P-thr) mimetics or surrogates may be used as extenders in the present invention to identify fragments that interact with subsites nearby to improve specificity or affinity for a target phosphatase. Thus extended tethering using known substrates or inhibitors as "anchors" to find nearby fragments by standard covalent tethering with the extender is one preferred embodiment of the instant invention.

Phosphotyrosine (P-tyr) mimetics are examples of SME's that may be customized for phosphatases like PTP-1B, LAR etc. Known PTP-1B P-tyr mimetics derivitized with mercapto-propanoic acid and/or cysteamine or the protected forms thereof, shown below, bind to the active site of a PTP-1B cys mutant.

Such a compound may be used as a dynamic extender to select a second fragment by covalent tethering as described above. The compound shown above when bound to the target and titrated against β-mercaptoethanol (BME) displays a BME$_{50}$ (the concentration of β-mercaptoethanol that, at equalibrium, is capable of displacing 50% of the bound compound from the target) of about 2.5 mM. When using a dynamic extender it is preferred to measure the BME$_{50}$ for the dynamic extender and to screen for a second fragment by covalent tethering at a total thiol concentration (BME+library thiols) at or below the BME$_{50}$ of the dynamic extender. For example, with the dynamic extender shown above having a BME$_{50}$ of 2.5 mM, the total thiol concentration in the second fragment screening step should be 2.5 mM or less and more preferrabley about 2 fold less, e.g. about 1 mM or less. Alternatively the dynamic extenter may be converted to a static extender removing the second fragment screening total thiol concentration issue. When converting a dynamic extender to a static extender it is important to maintain the same atom count so that non-covalent binding of the static extender to the target will not be distorted. For similar reasons it is important to minimize introduction of other other bulky atoms or groups. With these factors in mind, the above dynamic extender may be converted into the static extenders defined below.

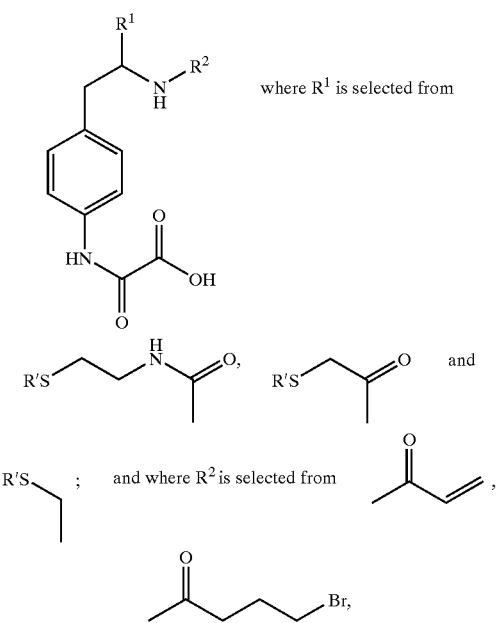

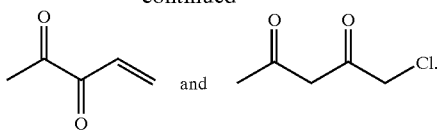

In still another embodiment of the invention, an extender may be a peptide either reversibly or irreversibly bound to the TBM. In this embodiment the peptide is from about 2–15 residues long, preferable from 5 to 10 residues, and may be composed of natural and/or artificial alpha amino acids. An example of such a peptide extender is an alpha helical p53 fragment peptide (or smaller known non-natural peptides) that are capable of binding to the N-terminal domain of MDM2 in a deep hydrophobic cleft with nM affinities. BCL-2 and BCL-xL are also known to contain deep peptide-binding grooves analogous the MDM2. Peptides that bind to these targets may also be useful peptide extenders according to the present invention. For example, a fragment peptide of p53 may form a reversible (e.g. disulfide) bond through an existing (e.g. cys) thiol or an introduced thiol (introduced cys, cysteamine derivatized with the carboxyl terminus or mercapto-propanoic acid through the amino terminus) on the peptide with an existing or introduced thiol on the TBM. In this case a TBM-peptide extender complex will be formed which is capable of being used to select a thiol or disulfide fragment from a subsequent covalent tether screen. This dynamic peptide extender will have one other free or protected thiol (e.g. one of the above not used to form the TBM-peptide extender complex), which is contacted with a library of thiol or protected thiol fragments under conditions suitable for forming a covalent disulfide bond with a fragment having affinity for the TBM. Optionally the peptide extender may be a static one where an irreversible covalent bond is formed with a nucleophile or electrophile on the TBM as described above. Optionally in this embodiment, a photoaffinity label may be used to attach the peptide extender to the TBM. As above, a free or protected thiol pre-existing or introduced is used to form a disulfide in a subsequent screen to find a small molecule fragment having affinity for the TBM.

Such a peptide extender may also be a synthetic peptide such as the "Z-WQPY" peptide where the TBM is the IL-1 receptor. Here, the peptide FEWTPGYWQPYALPL or fragments, mutants or analogues thereof can be used as a static or dynamic extender as described above to discover fragments via covalent tethering, where the disulfide tether is to or with the extender and the non-covalent bond is between the selected fragment and the TBM.

Other chemistries available for forming a reversible or irreversible covalent bond between reactive groups on a SME and a target or ligand, respectively, or between two ligands, are well known in the art, and are described in basic textbooks, such as, e.g. March, *Advanced Organic Chemistry*, John Wiley & Sons, New York, 4$^{th}$ edition, 1992. Reductive aminations between aldehydes and ketones and amines are described, for example, in March et al., supra, at pp. 898–900; alternative methods for preparing amines at page 1276; reactions between aldehydes and ketones and hydrazide derivatives to give hydrazones and hydrazone derivatives such as semicarbazones at pp. 904–906; amide bond formation at p. 1275; formation of ureas at p. 1299; formation of thiocarbamates at p. 892; formation of carbamates at p. 1280; formation of sulfonamides at p. 1296; formation of thioethers at p. 1297; formation of disulfides at p. 1284; formation of ethers at p. 1285; formation of esters at p. 1281; additions to epoxides at p. 368; additions to aziridines at p. 368; formation of acetals and ketals at p. 1269; formation of carbonates at p. 392; formation of denamines at p. 1264; metathesis of alkenes at pp. 1146–1148 (see also Grubbs et al., *Acc,Chem. Res.* 28:446–453 [1995]; transition metal-catalyzed couplings of aryl halides and sulfonates with alkanes and acetylenes, e.g. Heck reactions, at p.p. 717–178; the reaction of aryl halides and sulfonates with organometallic reagents, such as organoboron, reagents, at p. 662 (see also Miyaura et al., *Chem. Rev.* 95:2457 [1995]); organotin, and organozinc reagents, formation of oxazolidines (Ede et al., *Tetrahedron Letts.* 28:7119–7122 [1997]); formation of thiazolidines (Patek et al., *Tetrahedron Letts.* 36:2227–2230 [1995[); amines linked through amidine groups by coupling amines through imidoesters (Davies et al., *Canadian J. Biochem.c*50:416–422 [1972]), and the like. In particular, disulfide-containing small molecule libraries may be made from commercially available carboxylic acids and protected cysteamine (e.g. mono-BOC-cysteamine) by adapting the method of Parlow et al., *Mol. Diversity* 1:266–269 (1995), and can be screened for binding to polypeptides that contain, or have been modified to contain, reactive cysteines. All of the references cited in this section are hereby expressly incorporated by reference.

While it is usually preferred that the attachment of the SME does not denature the target, the TBM-SME complex may also be formed under denaturing conditions, followed by refolding the complex by methods known in the art. Moreover, the SME and the covalent bond should not substantially alter the three-dimensional structure of the target, so that the ligands will recognize and bind to a site of interest on the target with useful site specificity. Finally, the SME should be substantially unreactive with other sites on the target under the reaction and assay conditions.

5. Detection and Identification of Ligands Bound to a Target

The ligands bound to a target can be readily detected and identified by mass spectroscopy (MS). MS detects molecules based on mass-to-charge ratio (m/z) and thus can resolve molecules based on their sizes (reviewed in Yates, *Trends Genet.* 16: 5–8 [2000]). A mass spectrometer first converts molecules into gas-phase ions, then individual ions are separated on the basis of m/z ratios and are finally detected. A mass analyzer, which is an integral part of a mass spectrometer, uses a physical property (e.g. electric or magnetic fields, or time-of-flight [TOF]) to separate ions of a particular m/z value that then strikes the ion detector. Mass spectrometers are capable of generating data quickly and thus have a great potential for high-throughput analysis. MS offers a very versatile tool that can be used for drug discovery. Mass spectroscopy may be employed either alone or in combination with other means for detection or identifying the organic compound ligand bound to the target. Techniques employing mass spectroscopy are well known in the art and have been employed for a variety of applications (see, e.g., Fitzgerald and Siuzdak, *Chemistry & i Biology* 3: 707–715 [1996]; Chu et al., *J. Am. Chem. Soc.* 118: 7827–7835 [1996]; Siudzak, *Proc. Natl. Acad. Sci. USA* 91: 11290–11297 [1994]; Burlingame et al., *Anal. Chem.* 68: 599R–651R [1996]; Wu et al., *Chemistry & Biology* 4: 653–657 [1997]; and Loo et al., *Am. Reports Med. Chem.* 31: 319–325 [1996]).

However, the scope of the instant invention is not limited to the use of MS. In fact, any other suitable technique for the detection of the adduct formed between the biological target molecule and the library member can be used. For example, one may employ various chromatographic techniques such as liquid chromatography, thin layer chromatography and likes for separation of the components of the reaction mixture so as to enhance the ability to identify the covalently bound organic molecule. Such chromatographic techniques may be employed in combination with mass spectroscopy or separate from mass spectroscopy. One may optionally couple a labeled probe (fluorescently, radioactively, or otherwise) to the liberated organic compound so as to facilitate its identification using any of the above techniques. In yet another embodiment, the formation of the new bonds liberates a labeled probe, which can then be monitored. A simple functional assay, such as an ELISA or enzymatic assay may also be used to detect binding when binding of the extender or second fragment to the target occurs in an area essential for what the assay measures (e.g. binding to a "Hot Spot" in a protein:protein ELISA or binding in the substrate binding pocket for an enzyme assay). Other techniques that may find use for identifying the organic compound bound to the target molecule include, for example, nuclear magnetic resonance (NMR), capillary electrophoresis, X-ray crystallography, and the like, all of which will be well known to those skilled in the art.

6. Preparation of Conjugate Molecules (e.g. Diaphores)

Linker elements that find use for linking two or more organic molecule ligands to produce a conjugate molecule will be multifunctional, preferably bifunctional, cross-linking molecules that can function to covalently bond at least two organic molecules together via reactive functionalities possessed by those molecules. Linker elements will have at least two, and preferably only two, reactive functionalities that are available for bonding to at least two organic molecules, wherein those functionalities may appear anywhere on the linker, preferably at each end of the linker and wherein those functionalities may be the same or different depending upon whether the organic molecules to be linked have the same or different reactive functionalities. Linker elements that find use herein may be straight-chain, branched, aromatic, and the like, preferably straight chain, and will generally be at least about 2 atoms in length, more generally more than about 4 atoms in length, and often as many as about 12 or more atoms in length. Linker elements will generally comprise carbon atoms, either hydrogen saturated or unsaturated, and therefore, may comprise alkanes, alkenes or alkynes, and/or other heteroatoms including nitrogen, sulfur, oxygen, and the like, which may be unsubstituted or substituted, preferably with alkyl, alkoxyl, hydroxyalkyl or hydroxyalkyl groups. Linker elements that find use will be a varying lengths, thereby providing a means for optimizing the binding properties of a conjugate ligand compound prepared therefrom. The first organic compound that covalently bound to the target biomolecule may itself possess a chemically reactive group that provides a site for bonding to a second organic compound. Alternatively, the first organic molecule may be modified (either chemically, by binding a compound comprising a chemically reactive group thereto, or otherwise) prior to screening against a second library of organic compounds.

7. Compounds of the Invention

The compounds of the present invention are characterized by encompassing at least one, preferably at least two, ligands at least one of which has been identified by the extended tethering approach disclosed herein, and analogs of such compounds. Accordingly, the compounds of the present invention encompass numerous chemical classes, including but not limited to small organic molecules, peptides, (poly)nucleotides, (oligo)saccharides, etc. The ligands identified by the present methods typically serve as lead compounds for the development of further variants and derivatives designed by following well known techniques. In particular, the ligands identified (including monophores, diaphores, and more complex structures) are amenable to medicinal chemistry and affinity maturation, and can be rapidly optimized using structure-aided design. The present extended tethering approach is superior over other known techniques, including combinatorial chemistry, in that it allows further chemical modifications focused on ligands which have already been shown to to bind to different sites on a target, e.g. a TBM.

8. Uses of Compounds Identified

The method of the present invention is a powerful technique for generating drug leads, allows the identification of two or more fragments that bind weakly or with moderate binding affinity to a target at sites near one another, and the synthesis of diaphores or larger molecules comprising the identified fragments (monophores) covalently linked to each other to produce higher affinity compounds. The diaphores or similar multimeric compounds including further ligand compounds, are valuable tools in rational drug design, which can be further modified and optimized using medicinal chemistry approaches and structure-aided design.

The diaphores identified in accordance with the present invention and the modified drug leads and drugs designed therefrom can be used, for example, to regulate a variety of in vitro and in vivo biological processes which require or depend on the site-specific interaction of two molecules. Molecules which bind to a polynucleotide can be used, for example, to inhibit or prevent gene activation by blocking the access of a factor needed for activation to the target gene, or repress transcription by stabilizing duplex DNA or interfering with the transcriptional machinery.

9. Pharmaceutical Compositions

The ligands identified in accordance with the present invention, and compounds comprising such ligands, as well as analogues of such compounds, can be used in pharmaceutical compositions to prevent and/or treat a targeted disease or condition. The target disease or condition depends on the biological/physiological function of the target, e.g. TBM to which the ligand or the compounds designed based on such ligand(s) binds. Examples of such diseases and conditions are listed in the table of TBM's above.

Suitable forms of pharmaceutical compositions, in part, depend upon the use or route of entry, for example oral, transdermal, inhalation, or by injections. Such forms should allow the agent or composition to reach a target cell whether the target cell is present in a multicellular host or in culture. For example, pharmacological agents or compositions injected into the blood stream should be soluble. Other factors are known in the art, and include considerations such as toxicity and forms that prevent the agent or composition from exerting its effect.

The active ingredient, when appropriate, can also be formulated as pharmaceutically acceptable salts (e.g., acid addition salts) and/or complexes. Pharmaceutically acceptable salts are non-toxic at the concentration at which they are administered. Pharmaceutically acceptable salts include acid addition salts such as those containing sulfate, hydrochloride, phosphate, sulfonate, sulfamate, sulfate, acetate, citrate, lactate, tartarate, methanesulfonate, ethanesulfonate, benzenesulfonate, p-toluenesulfonate, cyclohexylsulfonate, cyclohexylsulfamate an quinate.

Pharmaceutically acceptable salts can be obtained from acids such as hydrochloric acid, sulfuric acid, phosphoric acid, sulfonic acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfonic acid, cyclohexylsulfamic acid, and quinic acid. Such salts may be prepared by, for example, reacting the free acid or base forms of the product with one or more equivalents of the appropriate base or acid in a solvent or medium in which the salt is insoluble, or in a solvent such as water, which is then removed in vacuo or by freeze-drying or by exchanging the ions of an existing salt for another ion on a suitable ion exchange resin.

Carriers or excipients can also be used to facilitate administration of the compound. Examples of carriers and excipients include calcium carbonate, calcium phosphate, various sugars such as lactose, glucose, or sucrose, or types of starch, cellulose derivatives, gelatin, vegetable oils, polyethylene glycols and physiologically compatible solvents. The compositions or pharmaceutical compositions can be administered by different routes including, but not limited to, intravenous, intra-arterial, intraperitoneal, intrapericardial, intracoronary, subcutaneous, intramuscular, oral topical, or transmucosal.

The desired isotonicity of the compositions can be accomplished using sodium chloride or other pharmaceutically acceptable agents such as dextrose, boric acid, sodium tartarate, propylene glycol, polyols (such as mannitol and sorbitol), or other inorganic or organic solutes.

Techniques and ingredients for making pharmaceutical formulations generally may be found, for example, in *Remington's Pharmaceutical Sciences*, 18$^{th}$ Edition, Mack Publishing Co., Easton, Pa. 1990. See also, Wang and Hanson "*Parental Formulations of Proteins and Peptides: Stability and Stabilizers,*" Journal of Parental Science and technology, Technical Report No. 10, Supp. 42-2S (1988). A suitable administration format can be best determined by a medical practitioner for each disease or condition individually, and also in view of the patient's condition.

Pharmaceutical compositions are prepared by mixing the ingredients following generally accepted procedures. For example, the selected components can be mixed simply in a blender or other standard device to produce a concentrated mixture which can then be adjusted to the final concentration and viscosity by the addition of water or thickening agent and possibly a buffer to control pH or an additional solute to control tonicity.

The amounts of various compounds for use in the compositions of the invention to be administered can be determined by standard procedures. Generally, a therapeutically effective amount is between about 100 mg/kg and $10^{-12}$ mg/kg depending on the age and size of the patient, and the disease or disorder associated with the patient. Generally, it is an amount between about 0.05 and 50 mg/kg of the individual to be treated. The determination of the actual dose is well within the skill of an ordinary physician.

10. Description of Preferred Embodiments

In a preferred embodiment, the methods of the present invention are used to identify low molecular weight ligands that bind to at least two different sites of interest on target proteins through intermediary disulfide tethers formed between a first ligand and the protein, and a reactive group on the first ligand and a second ligand, respectively.

The low molecular weight ligands screened in preferred embodiments of the invention will be, for the most part, small chemical molecules that will be less than about 2000 daltons in size, usually less than about 1500 daltons in size, more usually less than about 750 daltons in size, preferably less than about 500 daltons in size, often less than about 250 daltons in size, and more often less than about 200 daltons in size, although organic molecules larger than 2000 daltons in size will also find use herein. In one preferred embodiment, such small chemical molecules are small organic molecules, other than polypeptides or polynucleotides. In another preferred embodiment, the small organic molecules are non-polymeric, i.e. are not peptide, polypeptides, polynucleotides, etc.

Organic molecules may be obtained from a commercial or non-commercial source. For example, a large number of small organic chemical compounds are readily obtainable from commercial suppliers, such as Aldrich Chemical Co., Milwaukee, Wis. and Sigma Chemical Co., Sr. Louis, Mo., or may be obtained by chemical synthesis. The methods of the present invention are preferably used to screen libraries of small organic compounds carrying appropriate reactive group, preferably thiol or protected thiol groups.

In recent years, combinatorial libraries, typically having from dozens to hundreds of thousands of members, have become a major tool for ligand discovery and drug development. In general, libraries of organic compounds which find use herein will comprise at least 2 organic compounds, often at least about 25 different organic compounds, more often at least about 100 different organic compounds, usually at least about 300 different organic compounds, preferably at least about 2500 different organic compounds, and most preferably at least about 5000 or more different organic compounds. Populations may be selected or constructed such that each individual molecule of the population may be spatially separated from the other molecules of the population (e.g. in separate microtiter well) or two or more members of the population may be combined if methods for deconvolution are readily available. Usually, each member of the organic molecule library will be of the same chemical class (i.e. all library members are aldehydes, all library members are primary amines, etc.), however, libraries of organic compounds may also contain molecules from two or more different chemical classes.

In a preferred embodiment, the target biological molecule (TBM) is a polypeptide that contains or has been modified to contain a thiol group, protected thiol group or reversible disulfide bond. The TBM is then reacted with a Small Molecule extender (SME), which includes a portion having affinity for a first site of interest on the TBM and a group reactive with the thiol, protected thiol or reversible disulfide bond on the TBM. As discussed above, the linkage between the TBM and the SME may be either an irreversible covalent bond ("static" extended tethering), or a reversible covalent bond ("dynamic" extended tethering) to form a TBM-SME complex. Whether the static or dynamic approach is used, the TBM-SME complex is then used to screen a library of disulfide-containing monophores to identify a library member that has intrinsic affinity, most preferably the highest intrinsic affinity, for a second binding site (site of interest) on the target molecule. In a preferred embodiment, the reactive group on the modified TBM is a free thiol group contributed by the extender, and the library is made up of small molecular weight compounds containing reactive thiol group. For disulfide tethering to capture the most stable ligand, the reaction must be under rapid exchange to allow for equilibration. In a preferred embodiment, the reaction is carried out in the presence of catalytic amount of a reducing agent such as 2-mercaptoethanol. Thermodynamic equilibrium reached in the presence of a reducing agent will favor the formation of disulfide bond between thiol group of the extender on the modified TBM and thiol group of a member of the library having intrinsic affinity for the TBM. Thus, two different ligands with intrinsic affinity for two different sites on the same TBM will be covalently linked to form a diaphore. The diaphore will bind to the TBM with a higher affinity than any of the constituent monophore units. The monophore units in a diaphore may be from the same or different chemical classes. By "same chemical class" is meant that each monophore component is of the same chemical type, i.e., both are aldehyde or amines etc.

In a particular embodiment, the target can be present on a chip contacted with the ligand candidates. In this case, the covalent bond linking the first ligand to the target may be formed with the chip, in which case, the chip will become part of the covalent bond, representing a special class of "Small Molecule Extenders."

The library of the ligand candidates, e.g. small organic molecule ligands, can be attached to a solid surface, e.g. displayed on beads, for example as described in PCT publication WO 98/11436 published on Mar. 19, 1998. In a particular embodiment, beads are modified to introduce reactive groups, e.g. a low level of sulfhyrdyl groups. A library of ligand candidates is then synthesized on the modified beads. Subsequently, the library is incubated, under oxidizing conditions, with the target containing or modified to contain a reactive group, e.g. a sulfhydryl group such that s disulfide bond can be formed between the target and the sulfhydryl on the bead. The beads are then washed in the presence of a reducing agent, followed by incubation in the presence of a sulfhydryl quenching agent, such as iodoacetate. The beads may then be washed under denaturing conditions to remove any non-covalently bound target.

EXAMPLES

The invention is further illustrated by the following, non-limiting examples. Unless otherwise noted, all the standard molecular biology procedures are performed according to protocols described in (Molecular Cloning: A Laboratory Manual, vols. 1–3, edited by Sambrook, J., Fritsch, E. F., and Maniatis, T., Cold Spring Harbor Laboratory Press, 1989; Current Protocols in Molecular Biology, vols. 1–2, edited by Ausbubel, F., Brent, R., Kingston, R., Moore, D., Seidman, J. G., Smith, J., and Struhl, K., Wiley Interscience, 1987).

The concept of basic tethering approach has been described by Erlanson et al., supra, and in PCT Publication No. WO 00/00823. The "extended tethering" approach is illustrated in this application using caspase-3 as a target biological molecule (TBM). Caspases are a family of cysteine proteases, that are known to participate in the initiation and execution of programmed cell death (apoptosis). The first caspase (now referred to as Caspase-1) was originally designated as interleukin-1β-converting enzyme (ICE) (Thornburry et al., *Nature* 356:768–774 [1992]; Cerretti et al., *Science* 356:97–100 [1992]). Subsequently a large number of caspases have been identified and characterized forming a caspase family. Presently there are at least 10 members in the family (Caspase-1 to Caspase-10). Caspases are expressed in cells in an enzymatically inactive form and become activated by proteolytic cleavage in response to an apoptotic stimulus. The inactive proenzyme form consists of a large and a small domain (subunit), in addition to an inhibitory N-terminal domain. Caspase activation involves the processing of the proenzyme into the large and small subunits, which occurs internally within the molecule. Caspases are activated either by self-aggregation and auto-processing (as in the initiation of apoptosis), or via cleavage by an activated upstream caspase (as in the execution phase of apoptosis). For review, see, for example, Cohen G. M. *Biochem. J.* 326: 1–16 (1997).

Figure 4:
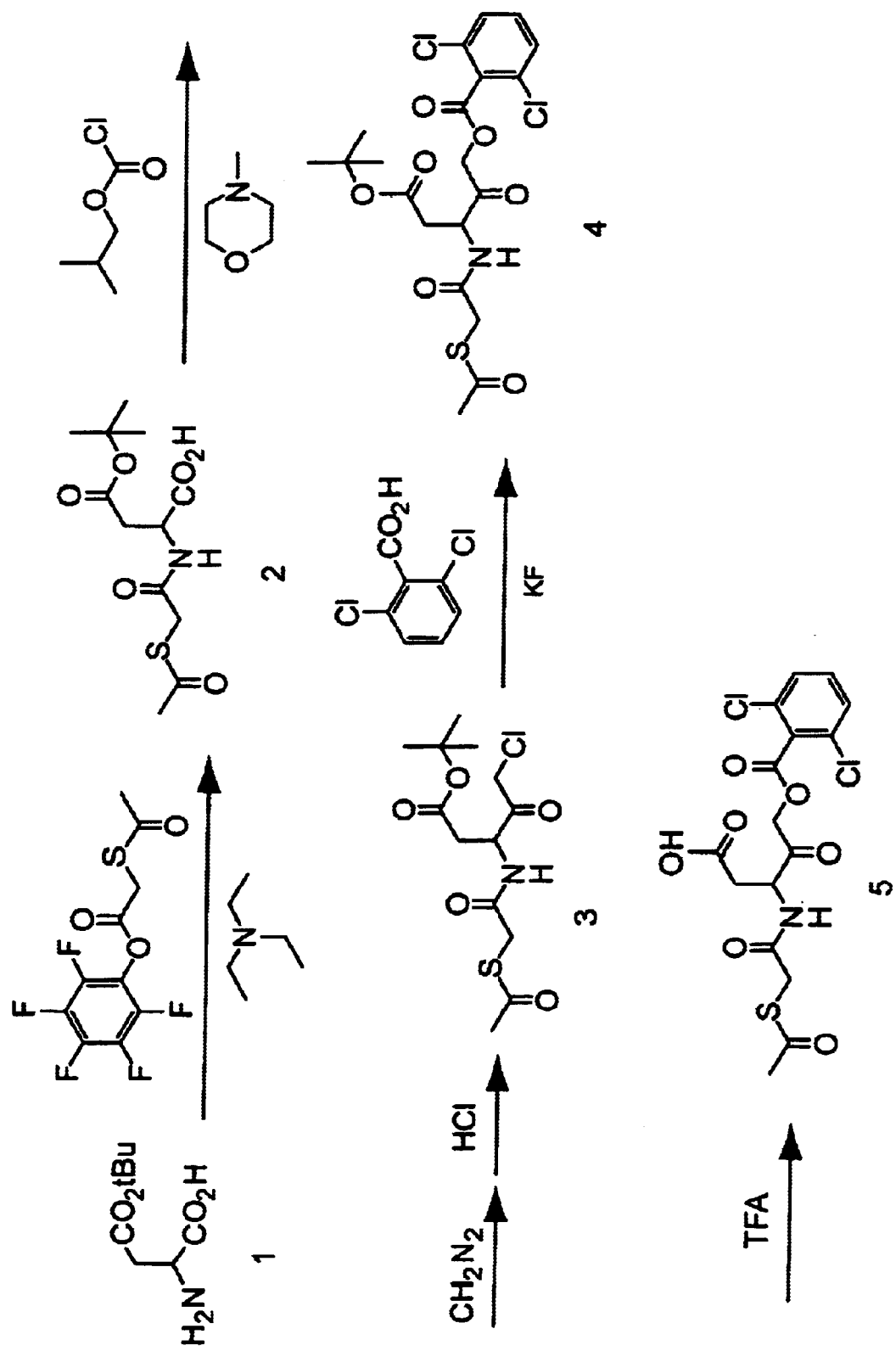
FIG. 4 illustrates the chemical synthesis of a specific extender (2,6-dichloro-benzoic acid 3-(2-acetylsulfanyl-acetylamino)-4-carboxy-2-oxo-butyl ester), as described in Example 2.
Figure 5:
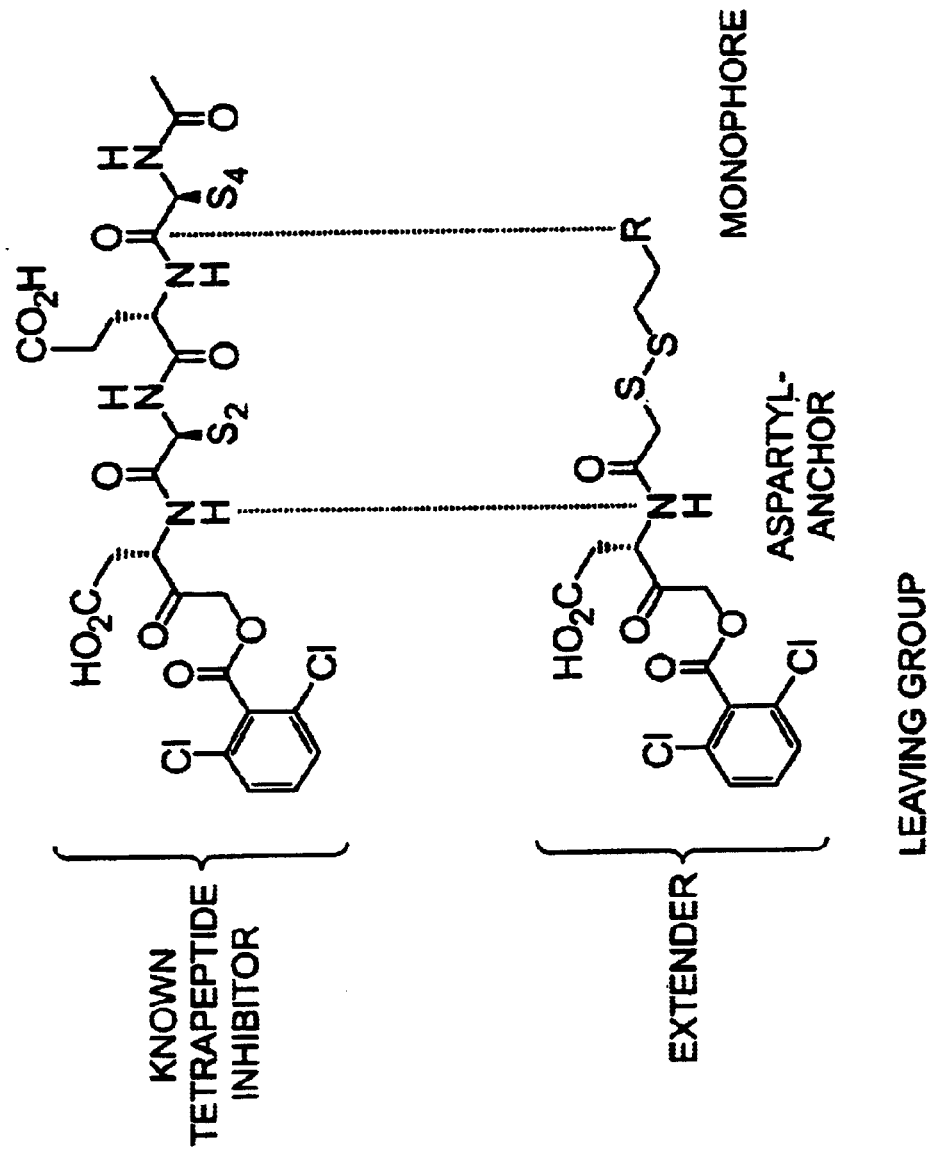
FIG. 5 shows the structural comparison between a known tetrapeptide inhibitor of Caspase-3 and a generic extender synthesized based on the inhibitor.

Based on a known tetrapeptide inhibitor of caspase (Ator and Dolle, *Current Pharmaceutical Design* 1:191–210 (1995)), an extender was synthesized: 2,6-Dichloro-benzoic acid 3-(2-acetylsulfanyl-acetylamino)-4-carboxy-2-oxo-butyl ester (shown as compound 5 in FIG. 4), the synthesis of which is described in Example 2 below. A generic structure of extender is shown in FIG. 4. Caspase was modified by reacting with the extender (Example 3) and subsequently used as a biological target molecule for screening of disulfide library prepared as described in Example 1, by using the extended tethering approach.

All commercially available materials were used as received. All synthesized compounds were characterized by $^1$H NMR [Bruker (Billerica, Mass.) DMX400 MHz Spectrometer] and HPLC-MS (Hewlett-Packard Series 1100 MSD).

Example 1

Disulfide Libraries

Disulfide libraries were synthesized using standard chemistry from the following classes of compounds: aldehydes, ketones, carboxylic acids, amines, sulfonyl chlorides, isocyanates, and isothiocyanates. For example, the disulfide-containing library members were made from commercially available carboxylic acids and mono-N-(tert-butoxycarbonyl)-protected cystamine (mono-BOC-cystamine) by adapting the method of Parlow and coworkers (Parlow and Normansell, *Mol. Diversity* 1: 266–269 [1995]). Briefly, 260 μmol of each carboxylic acid was immobilized onto 130 μmol equivalents of 4-hydroxy-3-nitrobenzophenone on polystyrene resin using 1,3-diisopropylcarbodiimide (DIC) in N,N-dimethylformamide (DMF). After 4 h at room temperature, the resin was rinsed with DMF (×2), dichloromethane (DCM, ×3), and tetrahydrofuran (THF, ×1) to remove uncoupled acid and DIC. The acids were cleaved from the resin via amide formation with 66 μmol of mono-BOC protected cystamine in THF. After reaction for 12 h at ambient temperature, the solvent was evaporated, and the BOC group was removed from the uncoupled half of each disulfide by using 80% trifluoroacetic acid (TFA) in DCM. The products were characterized by HPLC-MS, and those products that were substantially pure were used without further purification. A total of 530 compounds were made by using this methodology.

Libraries were also constructed from mono-BOC-protected cystamine and a variety of sulfonyl chlorides, isocyanates, and isothiocyanates. In the case of the sulfonyl chlorides, 10 μmol of each sulfonyl chloride was coupled with 10.5 μmol of mono-BOC-protected cystamine in THF (with 2% diisopropyl ethyl amine) in the presence of 15 mg of poly(4-vinyl pyridine). After 48 h, the poly(4-vinylpyridine) was removed via filtration, and the solvent was evaporated. The BOC group was removed by using 50% TFA in DCM. In the case of the isothiocyanates, 10 μmol of each isocyanate or isothiocyanate was coupled with 10.5 μmol of mono-BOC-protected cystamine in THF. After reaction for 12 h at ambient temperature, the solvent was evaporated, and the BOC group was removed by using 50% TFA in DCM. A total of 212 compounds were made by using this methodology.

Finally, oxime-based libraries were constructed by reacting 10 μmol of specific aldehydes or ketones with 10.5 μmol of HO(CH$_2$)$_2$S—S(CH$_2$)$_2$ONH$_2$ in 1:1 methanol/chloroform (with 2% acetic acid added) for 12 h at ambient temperature to yield the oxime product. A total of 448 compounds were made by using this methodology.

Individual library members were redissolved in either acetonitrile or dimethyl sulfoxide to a final concentration of 50 or 100 mM. Aliquots of each of these were then pooled into groups of 8–15 discrete compounds, with each member of the pool having a unique molecular weight.

Example 2

Extender (SME) Synthesis

For extended tethering approach, extender (2,6-Dichloro-benzoic acid 3-(2-acetylsulfanyl-acetylamino)-4-carboxy-2-oxo-butyl ester, shown as compound 5 in FIG. 4) was synthesized using a series of chemical reactions as shown in FIG. 4, and described below.

Synthesis of 2-(2-Acetylsulfanyl-acetylamino)-succinic acid 4-tert-butyl ester (compound 2, FIG. 4)

Acetylsulfanyl-acetic acid pentafluorophenyl ester (1.6 g, 5.3 mmol) and H-Asp(OtBu)—OH (1 g, 5.3 mmol) were mixed in 20 ml of dry dichloromethane (DCM). Then 1.6 ml of triethylamine (11.5 mmol) was added, and the reaction was allowed to proceed at ambient temperature for 3.5 hours. The organic layer was then extracted with 3×15 ml of 1 M sodium carbonate, the combined aqueous fractions were acidified with 100 ml of 1 M sodium hydrogensulfate and extracted with 3×30 ml ethyl acetate. The combined organic fractions were then rinsed with 30 ml of 1 M sodium hydrogensulfate, 30 ml of 5 M NaCl, dried over sodium sulfate, filtered, and evaporated under reduced pressure to yield 1.97 g of a nearly colorless syrup which was used without further purification. MW=305 (found 306, M+1).

Synthesis of 3-(2-Acetylsulfanyl-acetylamino)-5-chloro-4-oxo-pentanoic acid tert-butyl ester (compound 3, FIG. 4)

The free acid (compound 2) was dissolved in 10 ml of dry tetrahydrofuran (THF), cooled to 0° C., and treated with 0.58 ml N-methyl-morpholine (5.3 mmol) and 0.69 isobutylchloroformate. Dense white precipitate immediately formed, and after 30 minutes the reaction was filtered through a glass frit and transferred to a new flask with an additional 10 ml of THF. Meanwhile, diazomethane was prepared by reacting 1-methyl-3-nitro-1-nitrosoguanidine (2.3 g, 15.6 mmol) with 7.4 ml of 40% aqueous KOH and 25 ml diethyl ether for 45 minutes at 0° C. The yellow ether layer was then decanted into the reaction containing the mixed anhydride, and the reaction allowed to proceed while slowly warming to ambient temperature over a period of 165 minutes. The reaction was cooled to 8° C., and 1.5 ml of 4 N HCl in dioxane (6 mmol total) was added dropwise. This resulted in much bubbling, and the yellow solution became colorless. The reaction was allowed to proceed for two hours while gradually warming to ambient temperature and then quenched with 1 ml of glacial acetic acid. The solvent was removed under reduced pressure and the residue redissolved in 75 ml ethyl acetate, rinsed with 2×50 ml saturated sodium bicarbonate, 50 ml 5 M NaCl, dried over sodium sulfate, filtered, and evaporated to dryness before purification by flash chromatography using 90:10 chloroform:ethyl acetate to yield 0.747 g of light yellow oil (2.2 mmol, 42% from (1)). Expected MW=337.7, found 338 (M+1).

Synthesis of 2,6-Dichloro-benzoic acid 3-(2-acetylsulfanyl-acetylamino)-4-tert-butoxycarbonyl-2-oxo-butyl ester (compound 4, FIG. 4)

The chloromethylketone (compound 3) (0.25 g, 0.74 mmol) was dissolved in 5 ml of dry N,N-dimethylformamide (DMF), to which was added 0.17 g 2,6-dichlorobenzoic acid (0.89 mmol) and 0.107 g KF (1.84 mmol). The reaction was allowed to proceed at ambient temperature for 19 hours, at which point it was diluted with 75 ml ethyl acetate, rinsed with 2×50 ml saturated sodium bicarbonated, 50 ml 1 M sodium hydrogen sulfate, 50 ml 5 M NaCl, dried over sodium sulfate, filtered, and dried under reduced pressure to yield a yellow syrup which HPLC-MS revealed to be about 75% product and 25% unreacted (3). This was used without further purification. Expected MW=492.37, found 493 (M+1).

Synthesis of 2,6-Dichloro-benzoic acid 3-(2-acetylsulfanyl-acetylamino)-4-carboxy-2-oxo-butyl ester (compound 5, FIG. 4)

The product of the previous step (compound 4) was dissolved in 10 ml of dry DCM, cooled to 0° C., and treated with 9 ml trifluoroacetic acid (TFA). The reaction was then removed from the ice bath and allowed to warm to ambient temperature over a period of one hour. Solvent was removed under reduced pressure, and the residue redissoved twice in DCM and evaporated to remove residual TFA. The crude product was purified by reverse-phase high-pressure liquid chromatography to yield 101.9 mg (0.234 mmol, 32% from (3)) of white hygroscopic powder. Expected MW=436.37, found 437 (M+1). This was dissolved in dimethylsulfoxide (DMSO) to yield a 50 mM stock solution.

Example 3

Modification of Caspase 3 with Extender

Figure 6:
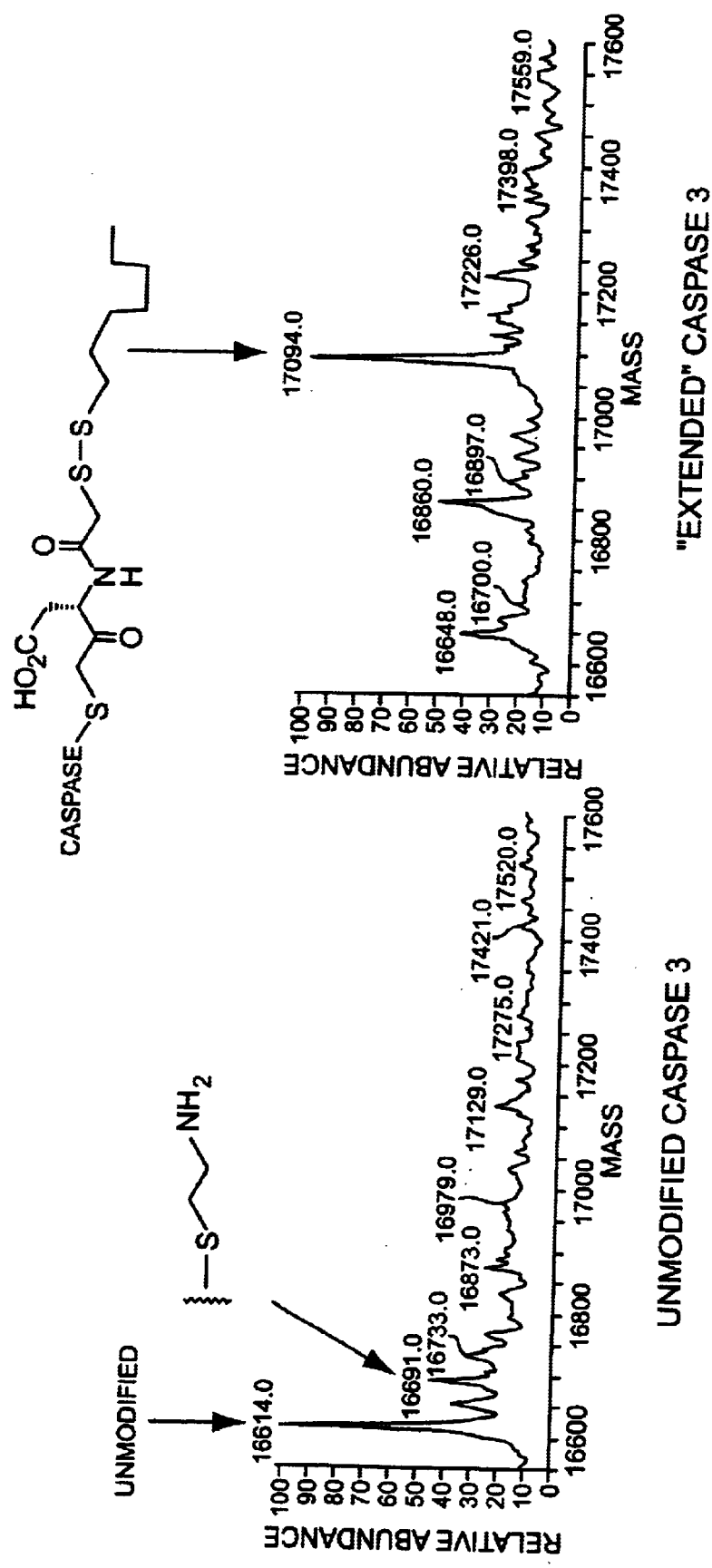
FIG. 6 shows mass spectra of two representative extended tethering experiments.

Caspase 3 was cloned, overexpressed, and purified using standard techniques (Rotonda et al., *Nature Structural Biology* 3(7):619–625 (1996)). To 2 ml of a 0.2 mg/ml Caspase 3 solution was added 10 ml of 50 mM 2,6-Dichloro-benzoic acid 3-(2-acetylsulfanyl-acetylamino)-4-carboxy-2-oxo-butyl ester (compound 5, FIG. 3) synthesized as described in Example 2, and the reaction was allowed to proceed at ambient temperature for 3.5 hours, at which point mass spectroscopy revealed complete modification of the caspase 3 large subunit (MW 16861Da, calculated MW 16860Da). The thioester was deprotected by adding 0.2 ml of 0.5 M hydroxylamine buffered in PBS buffer, and allowing the reaction to proceed for 18 hours, at which point the large subunit had a mass of 16819 Da (calculated 16818 Da). The protein was concentrated in a Ultrafree 5 MWCO unit (Millipore) and the buffer exchanged to 0.1 M TES pH 7.5 using a Nap-5 column (Amersham Pharmacia Biotech). The structure of the resulting "extended" caspase-3 is shown in FIG. 6.

The protein was then screened against a disulfide library prepared as described above, in Example 1, and using the methodology described in Example 4 below.

Example 4

Screening of Disulfide Library

In a typical experiment, 1 µl of a DMSO solution containing a library of 8-15 disulfide-containing compounds was added to 49 µl of buffer containing extender-modified protein. When mass spectroscopy was used for the identification of the bound ligand, the compounds were chosen so that each has a unique molecular weight. For example, these molecular weights differ by at least 10 atomic mass units so that deconvolution is unambiguous. Although pools of 8–15 disulfide-containing compounds were typically chosen for screening because of the ease of deconvolution, larger pools can also be used. The protein was present at a concentration of ~15 µM, each of the disulfide library members was present at ~0.2 mM, and thus the total concentration of all disulfide library members was ~2 mM. The reaction was done in a buffer containing 25 mM potassium phosphate (pH 7.5) and 1 mM 2-mercaptoethanol, although other buffers and reducing agents can be used. The reactions were allowed to equilibrate at ambient temperature for at least 30 min. These conditions can be varied considerably depending on the ease with which the protein ionizes in the mass spectrometer, the reactivity of the specific cysteine(s), etc.

After equilibration of aspartyl-conjugated caspase-3 (Example 3) and library (Example 1), the reaction was injected onto an HP1100 HPLC and chromatographed on a $C_{18}$ column attached to a mass spectrometer (Finnigan-MAT LCQ, San Jose, Calif.). The multiply charged ions arising from the protein were deconvoluted with available software (XCALIBUR) to arrive at the mass of the protein. The identity of any library member bonded through a disulfide bond to the protein was then easily determined by subtracting the known mass of the unmodified protein from the observed mass. This process assumes that the attachment of a library member does not dramatically change the ionization characteristics of the protein itself, a conservative assumption because in most cases the protein will be at least 20-fold larger than any given library member. This assumption was confirmed by demonstrating that small molecules selected by one protein are not selected by other proteins.

The results of a representative experiment are shown in FIG. 6. The spectrum on the right side of FIG. 6 shows the result of reacting "extended" Casase-3 (synthesized as described in Example 3), with a disulfide-containing molecule identified from a pool as modifying extended Caspase-3. The predominant peak obtained (mass of 17,094) corresponds to Caspase-3 covalently linked to the small molecule ligand which has an intrinsic affinity for a second site of interest on Caspase-3, resulting in the diaphore compound shown above the peak.

The mass spectrum shown on the left side is a deconvoluter mass spectrum of unmodified Caspase-3 (a cysteine-containing polypeptide target), and the same disulfide-containing small molecule ligand used above. The spectrum reveals a predominant peak corresponding to the mass of unmodified Caspase-3 (16,614 DA). A significantly smaller peak represents Caspase-3 disulfide-bonded to 2-aminoethanethiol (combined mass: 16,691 Da). Note that here the small molecule ligand is not selected because its binding site is too far from the reactive cysteine and no extender has introduced.

The initial lead compound, identified as describe above, was then modified in order to evaluate the relative importance of various substituents in specific binding to Caspase-3.

All references cited throughout the specification are hereby expressly incorporated by reference.

While the present invention has been described with reference to the specific embodiment thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the object, spirit and scope of the present invention. All such modifications are intended to be within the scope of the claims appended hereto.

What is claimed is:

1. A process comprising the steps of: (i) contacting a Target Biological Molecule (TBM) having a first and a second site of interest, and containing or modified to contain a nucleophile, selected from the group consisting of thiol, protected thiol, reversible disulfide, hydroxyl, protected hydroxyl, amino, protected amino, carboxyl and protected carboxyl groups, at or near the first site of interest, with a plurality of first organic ligand candidates, said candidates having a functional group reactive with the nucleophile, under conditions such that a reversible covalent bond is formed between the nucleophile and a candidate that has affinity for the first site of interest, to form a TMB-first ligand complex; (ii) identifying the first ligand from the TBM-first ligand complex; (iii) designing a derivative of the first ligand identified in (ii) to provide a small molecule extender (SME) having a first functional group reactive with the nucleophile on the TBM and a second functional group reactive with a second ligand having affinity for the second site of interest, wherein said first functional group is capable of forming an irreversible covalent group with the thiol, protected thiol, reversible disulfide bond, hydroxyl, protected hydroxyl, amino, protected amino, carboxyl or protected carboxyl group on said TBM; (iv) contacting the SME with the TBM to form a TBM-SME complex, and (v) contacting the TBM-SME complex with a plurality of second small organic ligand candidates, said candidates having a functional group reactive with the SME in said TBM-SME complex, wherein a candidate that has affinity for said second site of interest on said TBM forms a reversible covalent bond with said TBM-SME complex, whereby a second ligand is identified.

2. The process of claim 1 wherein the second functional group on said TBM and the functional group on said second ligand candidates in step (v) is a thiol, protected thiol or reversible disulfide group.

3. The process of claim 2 wherein step (v) is conducted under conditions of thiol exchange.

4. The process of claim 3 wherein said conditions are provided by a reducing agent selected from the group consisting of mercaptoethanol, dithiothreitol (DTT), dithio-erythreitol (DTE), mercaptopropanoic acid, glutathione, cysteamine, cysteine, tri(carbodiethyl)phosphine (TCEP), and tris(cyanoethyl)phosphine.

5. The process of claim 4 wherein said second ligand candidates in step (v) are members of a library.

6. The process of claim 5 wherein the library member having the highest affinity for said second site of interest on the TBM forms a disulfide bond with the TBM-SME complex.

7. The process of claim 1 comprising identifying said second ligand having affinity for said second site of interest on the TBM.

8. The process of claim 7 wherein said second ligand is identified by mass spectrometry (MS).

9. The process of claim 7 wherein said second ligand is identified by means of a detectable tag.

10. The process of claim 7, further comprising the step of synthesizing a molecule comprising said first and second ligands covalently linked to one another.

11. The process of claim 10 wherein said covalent linkage is provided by a disulfide bond.

12. The process of claim 11 wherein said molecule consists essentially of said first and second ligands, covalently linked through a disulfide bond.

13. The process of claim 12 further comprising the step of synthesizing derivatives of said molecule.

14. The process of claim 13 wherein the disulfide bond covalently linking the first and second ligands is replaced with a different covalent linkage.

15. A process comprising:
(i) providing a Target Biological Molecule (TBM) containing or modified to contain a reactive nucleophile near a first site of interest on the TBM;
(ii) contacting the TBM from (i) with a small molecule extender having a group reactive with the nucleophile on the TBM and having a free thiol or protected thiol;
(iii) adjusting the conditions of contacting in step (ii) to cause a covalent bond to be formed between the nucleophile on the TBM and the group on the small molecule extender thereby forming a covalent complex comprising the TBM and the small molecule extender, the complex displaying a free thiol or protected thiol near a second site of interest on the TBM;
(iv) contacting the complex from (iii) with a library of small organic molecules each molecule having a free thiol or exchangeable disulfide linking group, under conditions of thiol exchange wherein the library member having the highest affinity for the second site of interest on the TBM forms a disulfide bond with the complex; and
(v) identifying the library member from (iv).

16. The process of claim 15 further comprising the step of synthesizing a molecule consisting essentially of the small molecule extender having the electrophile group from step (ii) covalently linked through the disulfide with the library member identified in step (i).

17. The process of claim 16 further comprising the step of synthesizing a derivative of the molecule.

18. The process of claim 17 wherein the derivative contains a different group reactive with the nucleophile.

19. The process of claim 17 wherein the disulfide group covalently linking the small molecule extender with the library member identified in step (i) is replaced with a different group.

20. The process of claim 15 further comprising synthesizing a molecule consisting essentially of the small molecule extender without the group reactive with the nucleophile covalently linked through the disulfide with the library member identified in step (v).

21. The process of claim 20 further comprising replacing the disulfide, covalently linking the small molecule extender without the group reactive with the nucleophile with the library member identified in step (c), with a different group.

22. The process of claim 15 wherein the reactive nucleophile is a thiol.

23. The process of claim 22 further comprising, after step (i),
(a) contacting the TBM with a library of small organic molecules, each molecule having an exchangeable disulfide linking group, under conditions of thiol exchange wherein the library member having the highest affinity for the first site of interest forms a disulfide bond with the TBM;
(b) identifying the library member from (i); and
(c) forming a derivative of the library member in (ii) that is the small molecule extender having a group reactive with the nucleophile and having a thiol or protected thiol of step (b).

24. The process of claim 23 further comprising adding a disulfide reducing agent selected from the group consisting of mercaptoethanol, dithiothreitol (DTT), dithioerythreitol (DTE), mercaptopropanoic acid, glutathione, cysteamine cysteine, tri(carboxyethyl)phosphine (TCEP), and tris (cyanoethyl)phosphine.

25. The process of claim 15 wherein the identifying step comprises mass spectrum analysis.

26. The process of claim 23 wherein the identifying step comprises mass spectrum analysis.

27. The process of claim 23 wherein each molecule in the library of small organic molecules having an exchangeable disulfide linking group contains a cysteamine moiety.

* * * * *